(12) United States Patent
Carlsson et al.

(10) Patent No.: US 12,201,813 B2
(45) Date of Patent: Jan. 21, 2025

(54) MEDICAMENT DELIVERY DEVICE WITH EASILY CONNECTED DISPOSABLE AND REUSABLE UNITS

(71) Applicant: SHL MEDICAL AG, Zug (CH)

(72) Inventors: Daniel Carlsson, Enskede (SE); Daniel Säll, Segeltorp (SE)

(73) Assignee: SHL Medical AG, Zug (CH)

( * ) Notice: Subject to any disclaimer, the term of this patent is extended or adjusted under 35 U.S.C. 154(b) by 1049 days.

(21) Appl. No.: 16/968,350

(22) PCT Filed: Feb. 1, 2019

(86) PCT No.: PCT/EP2019/052471
§ 371 (c)(1),
(2) Date: Aug. 7, 2020

(87) PCT Pub. No.: WO2019/158372
PCT Pub. Date: Aug. 22, 2019

(65) Prior Publication Data
US 2021/0038817 A1    Feb. 11, 2021

(30) Foreign Application Priority Data

Feb. 19, 2018   (EP) .................................... 18157314

(51) Int. Cl.
*A61M 5/24*        (2006.01)
*A61M 5/315*       (2006.01)

(52) U.S. Cl.
CPC ....... *A61M 5/24* (2013.01); *A61M 2005/2492* (2013.01); *A61M 2005/31588* (2013.01); *A61M 2205/581* (2013.01); *A61M 2205/8206* (2013.01)

(58) Field of Classification Search
CPC ............ A61M 5/24; A61M 2005/2492; A61M 2005/31588; A61M 5/31571; A61M 5/31576; A61M 2005/2403; A61M 2005/2485; A61M 2005/2488; A61M 2005/2496

See application file for complete search history.

(56) References Cited

U.S. PATENT DOCUMENTS

| | | | |
|---|---|---|---|
| 2013/0184651 A1 | 7/2013 | Avery et al. | |
| 2013/0204203 A1 | 8/2013 | Mueller et al. | |
| 2013/0274655 A1* | 10/2013 | Jennings | A61M 5/3213 604/152 |
| 2014/0336589 A1 | 11/2014 | Sund et al. | |
| 2016/0228653 A1* | 8/2016 | Henley | A61M 5/3148 |
| 2016/0296702 A1 | 10/2016 | Rasmussen et al. | |

FOREIGN PATENT DOCUMENTS

| | | |
|---|---|---|
| CN | 102316917 A | 1/2012 |
| CN | 102427841 A | 4/2012 |
| CN | 102892446 A | 1/2013 |
| CN | 104136056 A | 11/2014 |
| CN | 105188807 A | 12/2015 |
| CN | 106029133 A | 10/2016 |
| JP | 2012-525185 A | 10/2012 |
| WO | 2010125400 A2 | 11/2010 |
| WO | 2012/085031 A1 | 6/2012 |
| WO | 2014/019997 A1 | 2/2014 |
| WO | 2014/037946 A1 | 3/2014 |
| WO | 2014/111370 A1 | 7/2014 |
| WO | 2015/18531 A1 | 2/2015 |

OTHER PUBLICATIONS

International Search Report and Written Opinion for Int. App. No. PCT/EP2019/05247, mailed Apr. 23, 2019.

* cited by examiner

*Primary Examiner* — Robert J Utama
*Assistant Examiner* — Neeraja Gollamudi
(74) *Attorney, Agent, or Firm* — McDonnell Boehnen Hulbert & Berghoff LLP

(57) ABSTRACT

An automatic medicament delivery device for auto injections that has a re-usable part containing a driving and a signal mechanism and a disposable part containing a syringe or a cartridge with a medicament. The parts can be interconnected simply in one axial move avoiding any rotation or turning. The device is easily and safely connected from two parts prior and during the injection process and automatically dissembled when the injection is completed allowing to remove the disposable part.

18 Claims, 24 Drawing Sheets

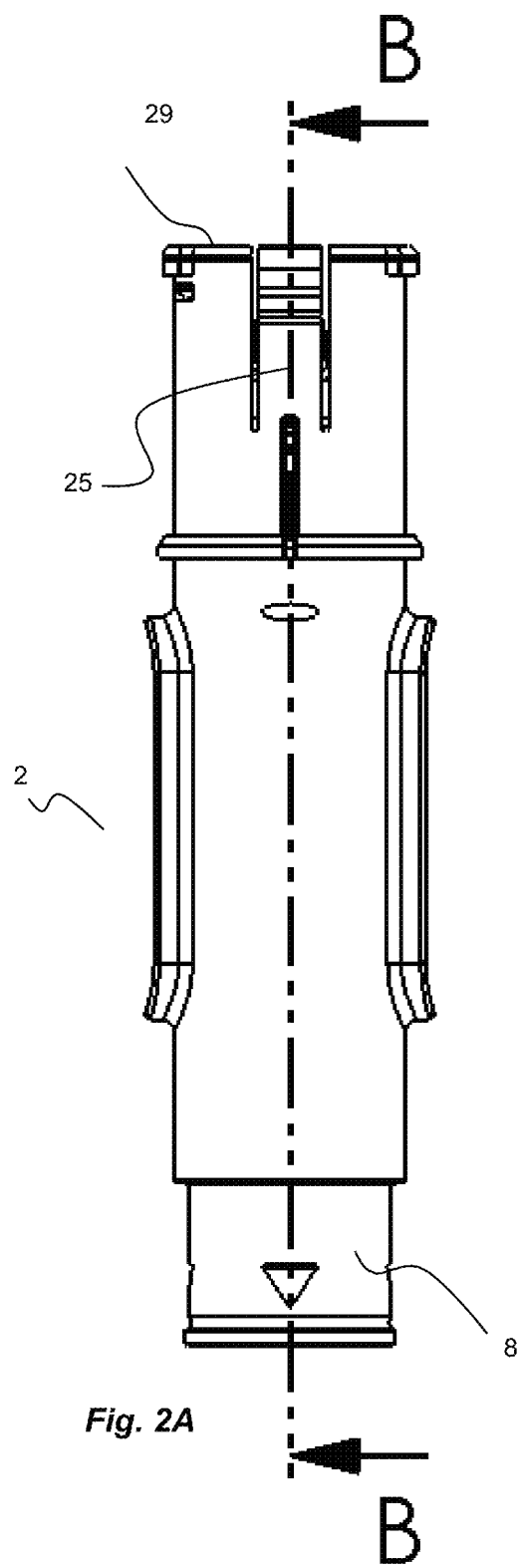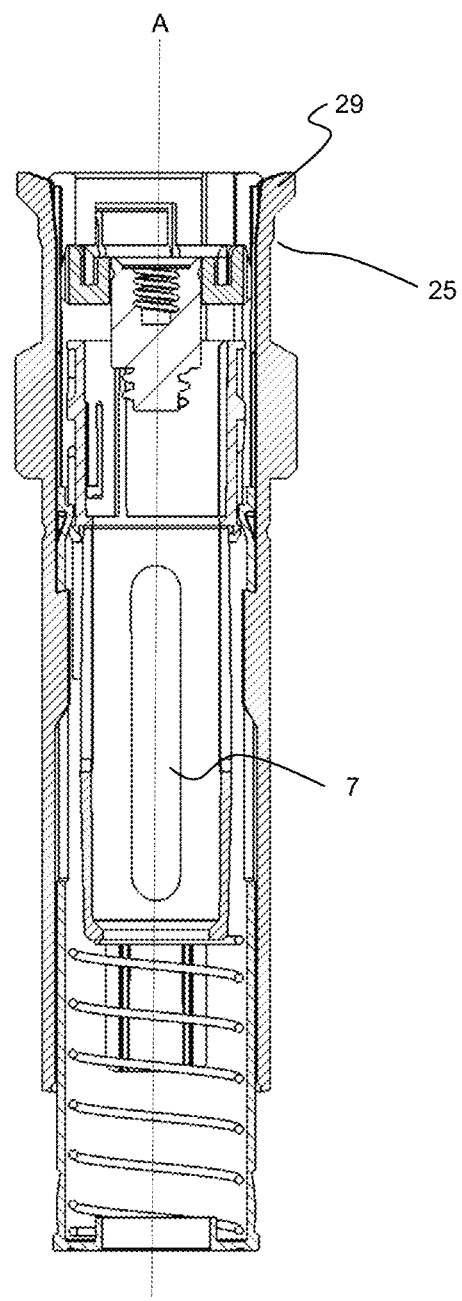
*Fig. 2A*   *Fig. 2B*

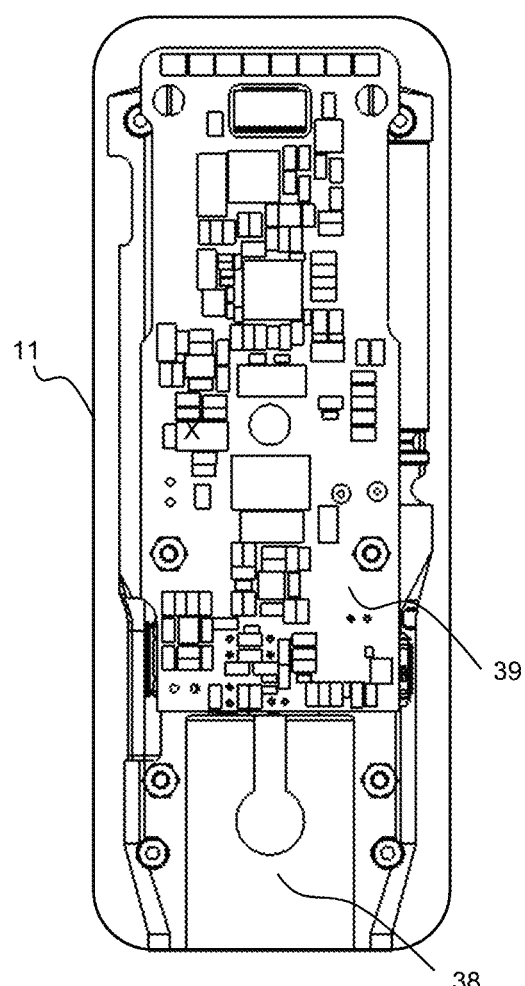
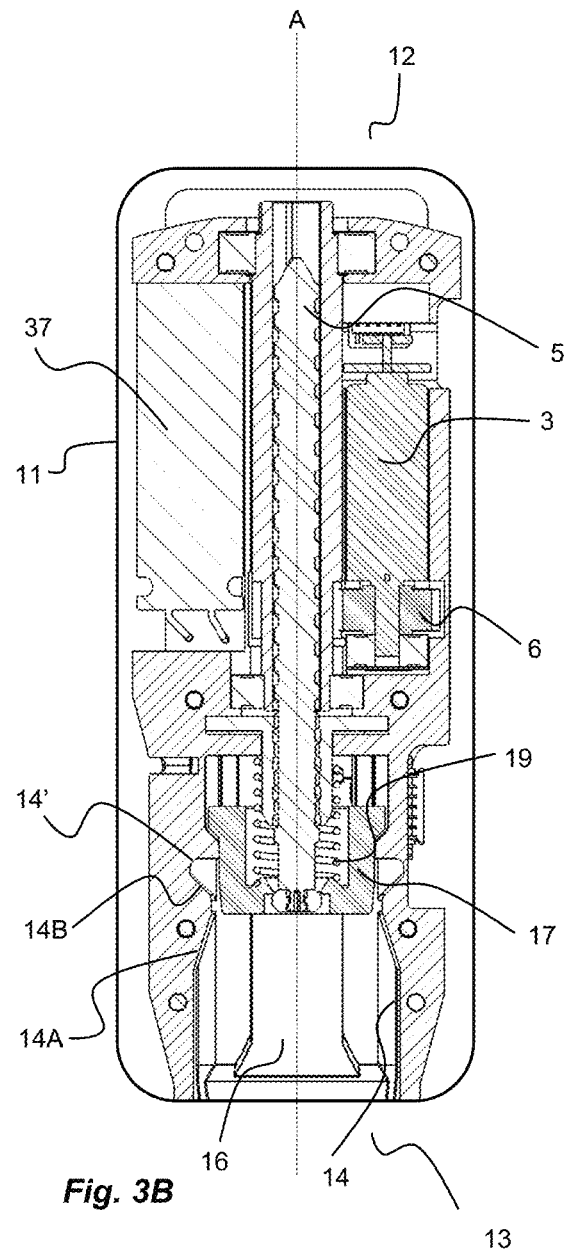
*Fig. 3A*
*Fig. 3B*

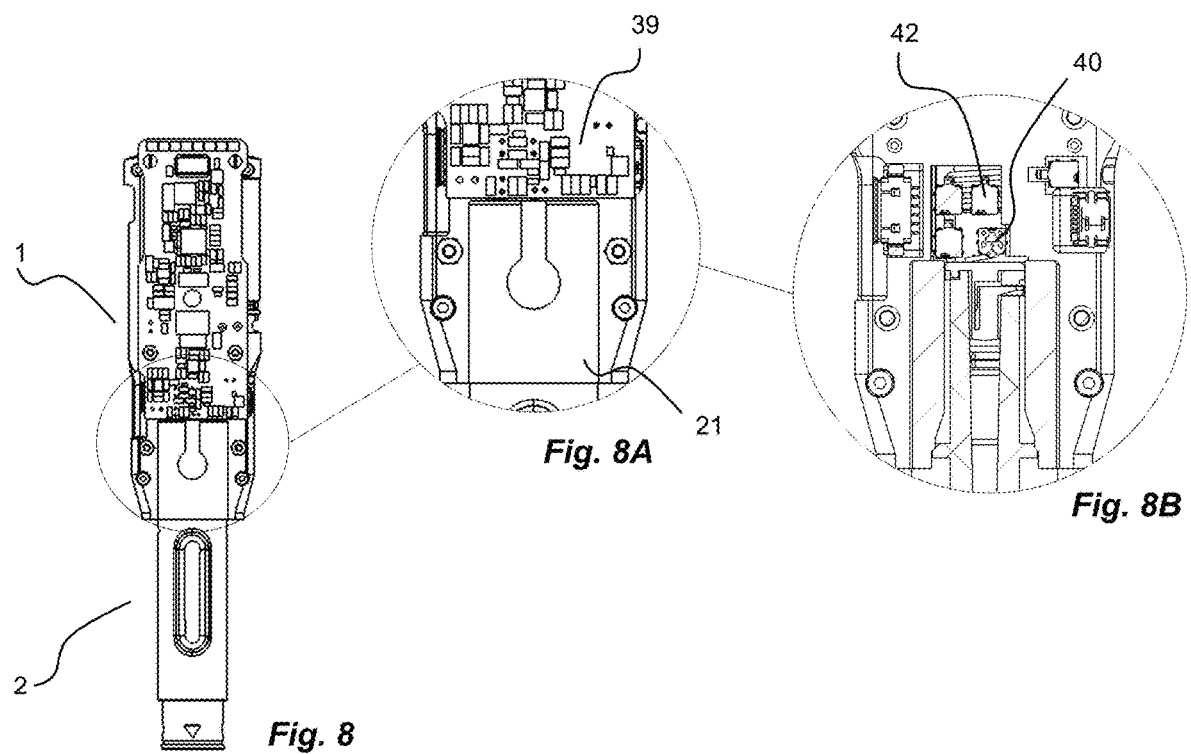

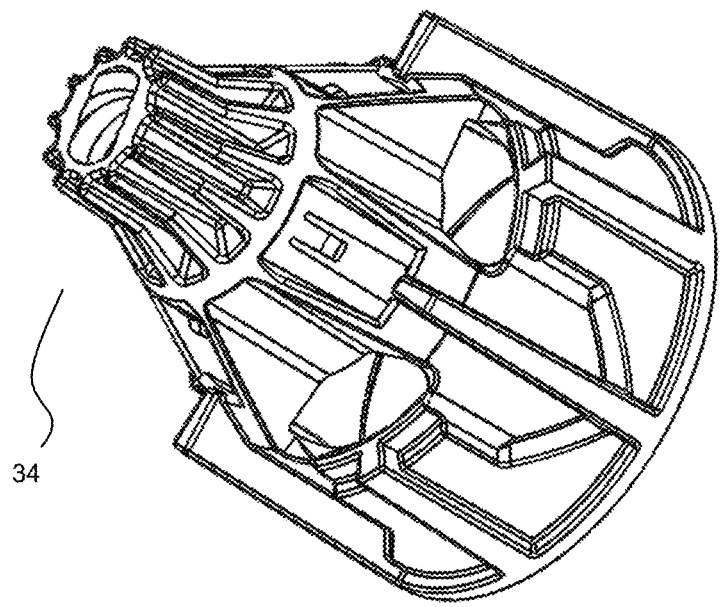
*Fig. 21A*
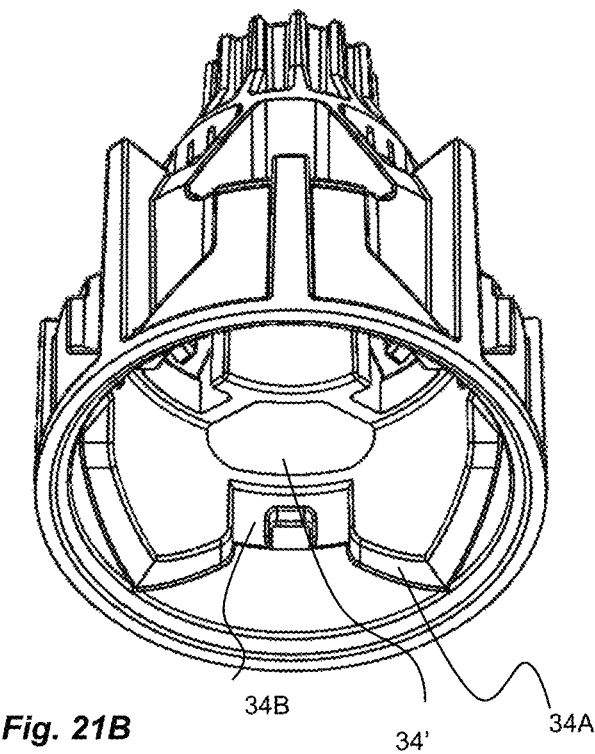
*Fig. 21B*   34B   34'   34A

MEDICAMENT DELIVERY DEVICE WITH EASILY CONNECTED DISPOSABLE AND REUSABLE UNITS

CROSS REFERENCE TO RELATED APPLICATIONS

The present application is a U.S. National Phase Application pursuant to 35 U.S.C. § 371 of International Application No. PCT/EP2019/052471 filed Feb. 1, 2019, which claims priority to European Patent Application No. 18157314.8 filed Feb. 19, 2018. The entire disclosure contents of these applications are herewith incorporated by reference into the present application.

TECHNICAL AREA

The disclosure relates to a medicament delivery device such as an injector or an automatic injector containing a syringe, a container or a cartridge with a medicament and used by untrained patients.

BACKGROUND

A number of the medicament delivery devices for self-administering of medicaments are out on the market and different design had been developed depending on which kind of medicament is to be delivered, in which dose etc. Often an automatic medicament delivery devices have two parts interconnected for the use.

One part, called a distal unit of the device, is usually comprises the driving mechanism such as a motor and/or a battery and thus can be re-used during a number of injections.

The other part, called a proximate or a disposable unit, is often containing or receiving the container with the medicament such as a syringe, a cartridge or the like, which then can be thrown away after the use of the medicament and substituted with the new one. These two parts' housings are to be interconnected by the user or patient for performing the injection and then to be disconnected in order to enable disposal of the proximate part after consumption of the medicament. The interconnection can be achieved in a number of different ways.

WO 2014/111370 discloses a bayonet connection type for assembling two parts of the medicament delivery device, when the user has to rotate the distal and proximate parts housings relative each other in order to achieve a connection there between.

WO2015/18531 teaches to apply threaded, bayonet and other types of connections for the connecting of two parts of the delivery devices but all those conventional types of connection require a complicated movement such as an axial inserting and simultaneously rotating one part relative the other. The complicated movement is not always desired and possible to perform for an untrained user and it might be difficult to handle the medicament delivery device.

WO2012/085031 discloses an automatic injection device, where a front-end part is attachable to a back-end part by insertion of a plunger of the back-part into the front-end part. The front-end part comprises also a mounting sleeve that is threaded on the front-end part and needed to be moved by the user hands/fingers towards the proximate medicament delivery end of the front-end part against a loading spring force for enabling the connection. When the sleeve is released, it locks the connection. This additional movement can be difficult to perform for the user with disabilities as requires quite a hand force and the user is needed to apply a sufficient force and perform a number of operations in order to connect the parts of the device together.

Therefore it is desired to enable the user assembly of the medicament delivery device much easier in a single move and insure that the device would not be disassembled by mistake prior the injection process is fully completed. It is desired to overcome above mentioned problems and drawbacks and provide a simple automatic connection in one movement of the two housings or parts of the medicament delivery device in reliable and safe way which is easy to handle for any user.

SUMMARY

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

Further, the term "longitudinal", with or without "axis", refers to a direction or an axis through the device or components thereof in the direction if the longest extension of the device and/or component.

Similarly, the terms "radial", "transversal" or "orthogonal" refers to a direction generally perpendicular to the longitudinal direction which is the axis direction and e.g. "radially or orthogonally outward" will refer to a direction pointing away for the longitudinal axis.

An object of this invention is provide a very simple and reliable way of automatically connecting the two parts or units of the medicament delivery in one axial movement which does not require any relative rotation of the parts and any other movements to be performed by the user hands or fingers. The first aspect of the invention is a novel simple axial connection of two units of the medicament delivery device such as a snap-connection type avoiding any rotation, twisting or turns.

According to an aspect of the invention, the object is achieved by a medicament delivery device according to claim 1.

According to embodiments, an automatic medicament delivery device has a longitudinal axis A, a first elongated unit with a distal closed end and an open connecting proximate end. The first unit might have a housing. The connecting end is surrounded by the housing of the unit. The first unit comprises a driving unit with a driving element able to move reciprocatingly. A second elongated unit with a housing is adapted to receive a medicament container (S, C) and has a first proximal medicament delivery end and a second distal connecting end. The distal connecting end of the second unit is adapted to be connected with the open proximate connecting end of the first unit only by insertion of the second connecting end into the open connecting end along the longitudinal axis A in one move avoiding any rotation and twisting. The one of the connecting ends of the units is equipped with at least one flexible part which is able to move orthogonally or radially inwards and outwards relative to the axis A due to force created by the insertion of the second connecting end into the open connecting end. A movable locking element is arranged inside the first unit or its housing coaxially and configured to interact with the flexible part due to a relative axial movement one of the flexible part and the locking element so as to lock and release the connecting ends of the units and/or the housings of the device relative each other.

According to a further aspect of the invention, the locking element is one of a separate axially movable element and a locking element integrated with one connecting end.

The flexible part is one of an integral part of one of a frame, a connecting end and a separate flexible part arranged on one of the connecting ends.

According to the invention, the snap-connection of the re-usable and the disposable units or their housings forming the medicament delivery device is achieved by a single axial motion of the one unit or housing relative the other one avoiding a rotation, twisting or turning the units or housings relative each other and not demanding any additional manipulation from the user.

Further the snap-connection might be secured, if desired, by the locking element which is situated inside the unit or its housing and is activated automatically depending on the medicament delivery device state. Therefore, the distal and the proximal units snap connection is not affected by the user's hand/fingers avoiding the mistakes. The internal automatically locking element prevents from an accidental disconnection of the device units or housings prior to the injection is started and/or completed. This operation provides a first connected state of the medicament delivery device. The first inserting and locking state of the device can be achieved in one single stage or two separate stages.

The device according to the invention is much easier to assemble by connecting the two housings for a none-trained user, just by pulling one disposable part or unit into the other re-usable part or unit axially excluding a rotation motion for the fixation of one to the other as required in the known connections. The user receives also a direct feedback by a snap connection click informing the user that the device units are firmly interconnected. The very important and advantageous feature also is that the user cannot by mistake dissemble the device in two pieces prior to the injection is fully completed as the locking process is performed automatically. This feature provides a safety for the device use and a security for the user.

These and other aspects of, and advantages with, the present invention will become apparent from the following detailed description of the invention and from the accompanying drawings.

BRIEF DESCRIPTION OF DRAWINGS

Various aspects of the invention, including its particular features and advantages, will be readily understood from the example embodiments discussed in the following detailed description and the accompanying drawings, in which:

FIG. 2A illustrates the disposable part, and FIG. 2B is a cross-section view of the disposable part illustrated in FIG. 2A;

FIGS. 3A and 3B illustrate two orthogonal cross-sectional views of the reusable part of the medicament delivery device according to the first embodiment provided with a housing;

FIG. 6F illustrates two conical connections between the interacting parts and FIG. 6G is a cross-sectional view perpendicular to the axis A.

FIG. 8 illustrates still another cross-sectional view of the medicament delivery device according to the first embodiment with connected together two units, where FIGS. 8A and 8B are enlarged cross-sectional views illustrating control sensors;

FIGS. 21A and 21B illustrate an isometric view of a holder which is used in the third embodiment of the medicament delivery device of the third embodiment;

DETAILED DESCRIPTION

Figure 1:
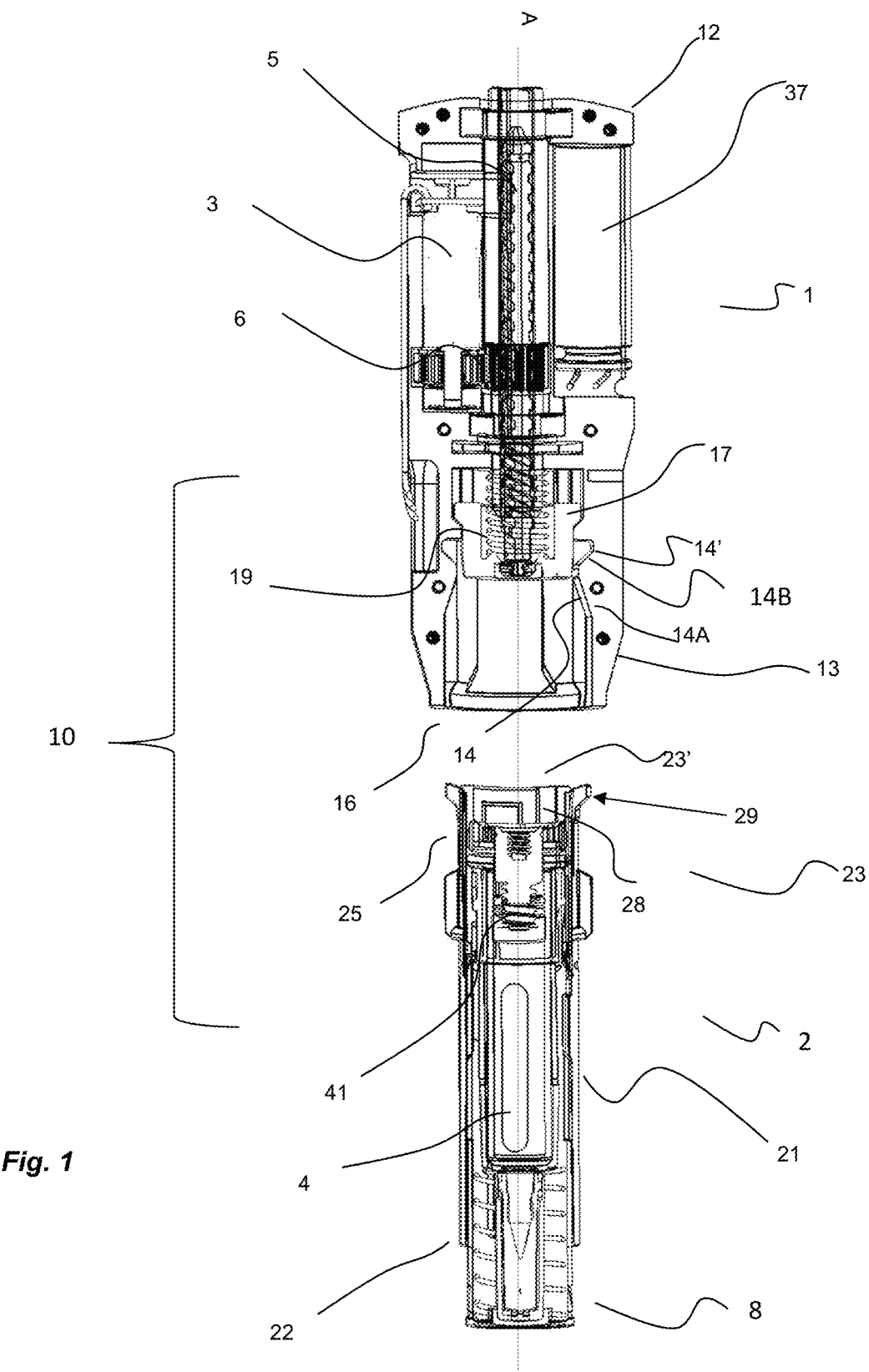
FIG. 1 illustrates a cross-sectional view of the medicament delivery device of the first embodiment of the invention for the device with two separate a disposable and a reusable parts to be assembled together for performing an injection.

In the following detailed description, reference is made to the accompanying drawings which forms a part thereof. In the drawings, the similar symbols typically identify the similar components, unless context dictates otherwise. Other embodiments may be utilised and other changes may be made within the scope of the subject matter presented herein.

The two parts or units of the medicament delivery device, a first back-end or a distal unit that is a reusable power pack or part and a second front-end or proximal unit that is a disposable drug cassette unit, shall be joined easily in a simple manner by any user including the users with different disabilities. The disposable part of the device, usually containing a medicament, is simply axially inserted into the other reusable part in one single move without a need then to be turned around for locking or other fixation and being fixed by so called snap-connection due to expanding of a flexible part(s) as known in the art.

Depending on the device design, the both medicament delivery device units, disposable and reusable ones, might have a separate outer housings mounted to include all the parts thereof or alternatively, the housing(s) can be formed integrally with a suitable outer part of the unit. At the insertion, when the units connecting ends or two housings are fixed relative each other by the snap locking. After that, this snap connection of the units might be further ensured or affixed by an additional automatic fixation by a locking element preventing a disengagement of the snap connected housings or the connecting ends until an injection is carried out completely or discontinued. This locking element provides a direct feed back to the user as an audible "click" signal. In the inventive solution, this locking element is always an internal element situated inside the housing or the unit so that it never can be manipulated by a user's fingers. This makes it impossible to disconnect the units by mistake or misuse prior the injection is completed. The locking and unlocking of these units relative each other occurs automatically without any need from the user to make any manipulation. This function increase a safety for the user. After the medicament is fully injected, the device allows to dissemble the two housings or units and the disposable part can be discarded and replaced at the next injection occasion. The disposable unit can be a single use or a multiple use unit. A need to dispose only a part of and not the entire medicament delivery device is an environmental advantage. Minimising of the disposal unit components, parts and materials according to the invention is also important for the environment.

FIG. 1 generally illustrates a first preferred embodiment of the medicament delivering device 10 for performing injections and having a first distal reusable part or unit 1 and a second proximate disposable part or unit 2.

The unit 1 has a longitudinal housing 11 as illustrated in FIG. 3B with a central longitudinal axis A. The unit 1 has a closed distal end 12 and an open connecting proximal end 13 on the opposite side in the axial direction.

The second proximal disposable unit 2 is illustrated in FIG. 2A and its longitudinal cross-section in a direction of the arrows B is illustrated in FIG. 2B. The unit 2 has a monitoring window 7 and comprises a container 4 with a medicament. The medicament container 4 is one of a syringe S and a cartridge C for a single or multiple delivery.

As can be seen in FIG. 2B, the second proximal disposable unit 2 has a fewer details than the reusable unit 1.

The unit 2 comprises a longitudinal housing 21 with a central axis A, which is the same axis for the unit 1 and its housing 11, a first medicament delivery end 22 and a second hollow connecting end 23 (FIG. 1). The unit 2 comprises a rear cup 28 on the connecting end 23 and a protecting cup 8 on the medicament delivery end 22 to cover and protect an injection needle 20 (not shown here). The housings 11, 21 can be of the same or different cross-section and dimensions.

Figure 5:
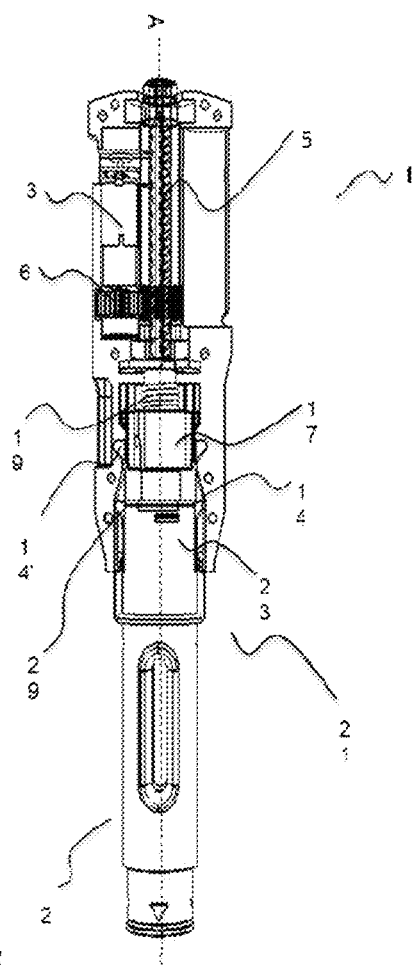
FIG. 5 illustrates a cross-sectional view of the medicament delivery device of the first embodiment according to the invention at the very beginning of an assembling process of the disposal and the reusable parts.
Figure 7:
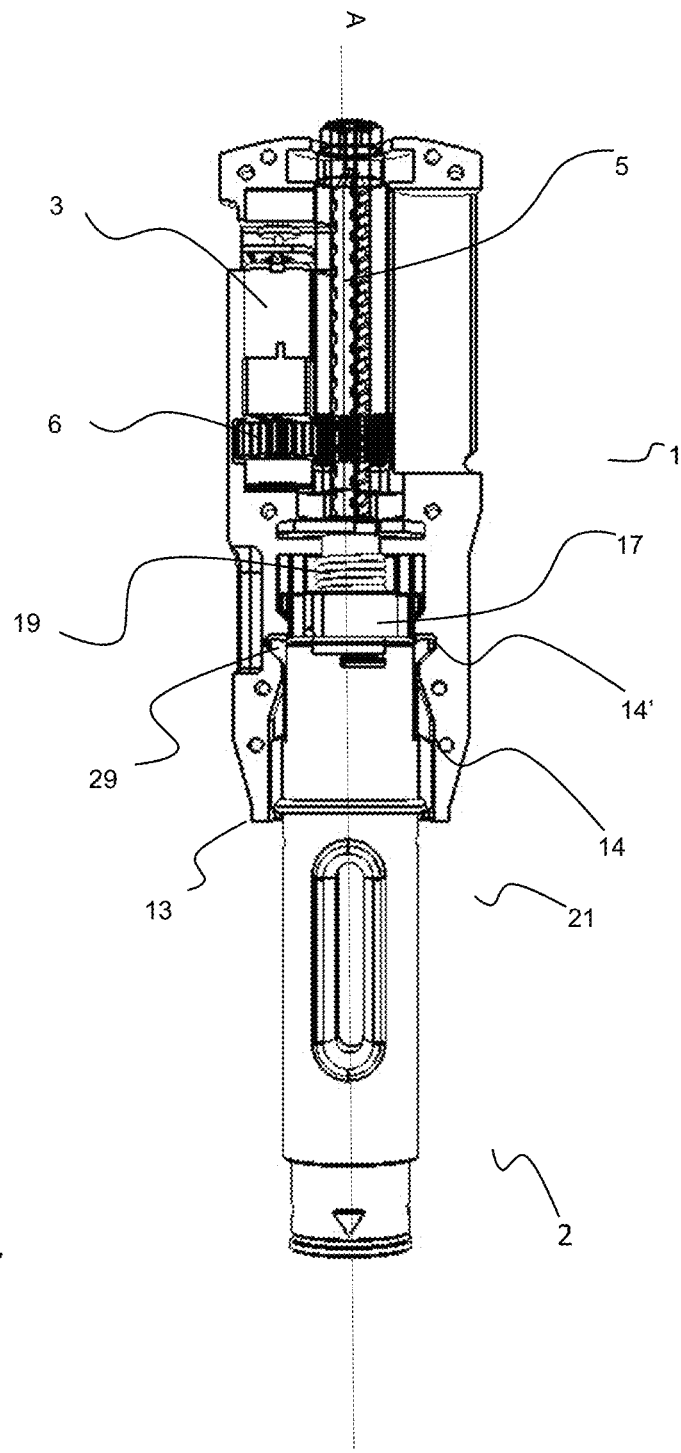
FIG. 7 illustrates a cross-sectional view of the medicament delivery device of the first embodiment with a firmly connected the first reusable unit or part and the second disposable unit or part of the device according the invention.

The unit 2 and/or the housing 21 of the unit 2 via the connecting end 23 is to be interconnected with the connecting end 13 of the unit 1 and/or the housing 11 of the unit 1 by insertion of the connecting end 23 into an axial receiving opening 16 of the connecting end 13 of the unit 1 along the common central axis A as illustrated in FIGS. 5 and 7. While not shown here, the housing 11 can form itself the connecting end 13 of the unit 1.

In this first embodiment, the connecting end 23 is to be inserted in the receiving opening 16 of the connecting end 13 of the first unit 1, but it is to be understood that verse visa the housing 11 of the unit 1 can be inserted into the housing of unit 2. The medicament container 4 is spaced within the housing 21 of the disposable unit 2.

Figure 4:
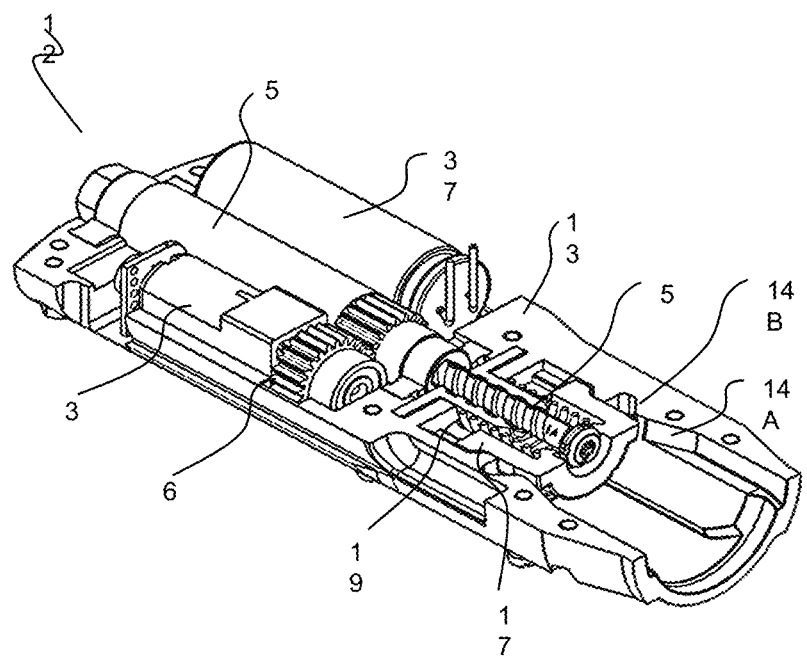
FIG. 4 illustrates an isometric view of the reusable part according to the first embodiment of the invention.

A geometry or profile of this inner surface 14 of the receiving axial opening 16 in the connecting end 13 of the unit 1 can have different cross-sections shapes and dimensions, seen orthogonally to the axis A and serves as a guiding surface 14 for insertion of the connecting end 23 of the housing 21 of the disposable unit 2 as illustrated in FIGS. 1 and 4.

The housing 21 of the proximal disposable unit 2 of the first embodiment has at its connecting end 23 at least one, but in this embodiment preferably at least two flexible parts 25 or flexing arms 25 as illustrated in FIGS. 2 and 6A-E, that are able to flex outwardly from and inwardly closer relative to the axis A moving radially and orthogonally to the axis A, when the connecting end 23 is to be inserted into the opening 16 of the connecting end 13 and an outer force is applied to them as illustrated in FIGS. 6A-6E showing the insertion sequences. Each flexible part 25 has a ledge 29 extended outwardly in the axial direction (see FIG. 1) at the end 23. The connecting end 23 of the housing 21 has the opening 23' on its end to be inserted into the housing 11.

The flexible parts 25 are able to move orthogonally inwardly and/or outwardly relative to the axis A, which means that the flexible parts the able to move radially e.g. flex in and out relative the axis A.

In this first embodiment, the flexible parts 25 are made as integral elements with the housing 21 at its connecting end 23 of the proximate disposable unit 2 in form of axially extending tongues 25 but any other embodiments are also possible. The flexible part 25 has a radially outwards or perpendicularly to the axis A extending ledge 29. The housing 21 is manufactured from a suitable plastic material with the required properties.

In the first embodiment, the opening 16 has an inner cylindrical shape surface 14 with a following first inclined part or surface 14A of a decreasing diameter and then another a second inclined part or surface 14B with an increasing diameter relative to the axis A forming the groove 14'. The first inclined part 14A guides the ledged 29 of the flexible parts 25 forcing them to move inwards orthogonally and the second inclined part 14B allows the flexible parts(s) 25 move orthogonally outwards fitting the extensions or ledges 29 into the groove 14'. The opening 16 has the circular groove 14' on its distal end in the axial direction towards the closed end 12. The groove 14' serves for receipting of the corresponding extension or ledge 29 on the housing 11 for performing the snap-locking between the housings 11 and 21 due to flexing out of the flexible part 25.

The groove 14' diameter is larger than the narrowest part or neck of the opening 16 and approximately is equal to the outer ledges 29 dimension. As the groove 14' having a larger diameter than the opening 16, at the insertion the flexible part 25 able to expand outwardly relative the axis A. In this way, a first stage of the preliminary connection of the both units 1, 2 and their housings 11, 21 can be automatically achieved due to expansions of the flexible parts 25.

A locking element 17 is additionally provided in order to ensure that the housings 11, 21 or the units 1 and 2 by default would not be dissembled by the user prior to or during the injection process. As the flexible parts 25 move radially at the end of the insertion, as illustrated in FIG. 6B, their contact with the locking element 17 terminates as illustrated in FIG. 6C, and the locking element 17 is forced by the compressed spring 19 into the opening 23' in the proximate end 13 direction. The user receives a clear signal such as the snap click of the established connection of the units 1, 2. The snap connection of the two units 1, 2 occurs due to flexibility of the flexible parts 25 and a corresponding geometry of the receiving interacting and interconnecting surfaces 14, 14A, 14B.

The locking element 17 is also manufactured from the suitable plastic material and arranged to interact with the flexible part 25 due to a relative axial movement one of the flexible part 25 and the locking element 17 so as to lock and release the connecting ends 13, 23 of the units 1, 2 relative each other. In some embodiments, the locking element 17 is connected to and moved by the plunger rod 5 reciprocatingly. In some embodiments this locking element might be eliminated substituted by the other equivalent means.

According to the first embodiment illustrated in FIGS. 1, 3B and 6A-6E, the locking element 17 is situated into a frame 38 and loaded in the disposable part 2 direction or in the direction of the opening 16 in the housing 11 by a spiral spring 19 placed around a driving element or a plunger rod 5. The spring 19 is placed between the locking element 17 and the driving unit 3 mounted on the frame 38. As illustrated in FIG. 3B, the spring 19 rests on the frame 38 and loads the locking element 17. The locking element 17 in this embodiment is formed as a locking ring 17 preventing the radial or orthogonal inwards movement of the flexible elements 25 when interacting with them and thus preventing a disengagement of the snap-connection of the units 1, 2, which will be explained later. The function of the locking element 17 is to ensure the proper locking of the snap connection between the housings 11 and 21, forming the medicament delivery device 10, prior to and during the injections process. The locking element 17 might have any other alternative embodiment for performing this function.

The locking element 17 of this embodiment is moved axially by the spring 19 when locking the units 1, 2 of the medicament delivery device 10 to each other and preparing the device 10 for an injection and is moved in the axial direction towards the closed distal end 12 by the plunger rod 5 when releasing the units 1 and 2 snap connection.

As illustrated in FIGS. 1 and 3B, a driving unit 3 is situated approximate to the closed end 12 inside the housing 11. The driving unit 3 via a transmission 6, presented here as gears 6, interacts with the driving element 5 such as the plunger rod 5.

The driving unit 3 might be one of any suitable type known in the art such as a mechanical, electromechanical, pneumatic or electrical driving or motor. The driving unit 3 may comprise one of a mechanical driving device 30, a pneumatic driving device 31 and an electrical driving device 32. In case of the electrical motor 32 is used, the device 10 or the driving unit 3 might be further equipped with a battery 37, for example of about 6 volts. The driving unit 3 is mounted on the frame 38 as illustrated in FIG. 3A and controlled by sensors of a printed circuit 39.

The electrical motor 32 is able to rotate in both directions, thus moving the plunger rod 5 reciprocatingly, and the plunger rod 5 motion is controlled by a number of sensors.

The plunger rod 5 is usually used for performing the injection process due to the rod 5 axial movement towards the disposal unit 2 and pushing on a plunger 41 of e.g. the syringe S, thus conducting the injection.

There are designs of the automatic medicament delivery devices where the plunger rod 5 is enable to move reciprocatingly: firstly towards the proximate end of the device 10 for performing the injection process and then return into the initial position moving towards the closed end 12.

The plunger rod 5 is arranged movably in the axial direction A primarily for activating the medicament delivery from the container 4 such as the cartridge C or the syringe S by interacting with the plunger 41 and secondly for assisting a dissembling of the units 1, 2 after the injection is completed as will be described later.

Figure 6A:
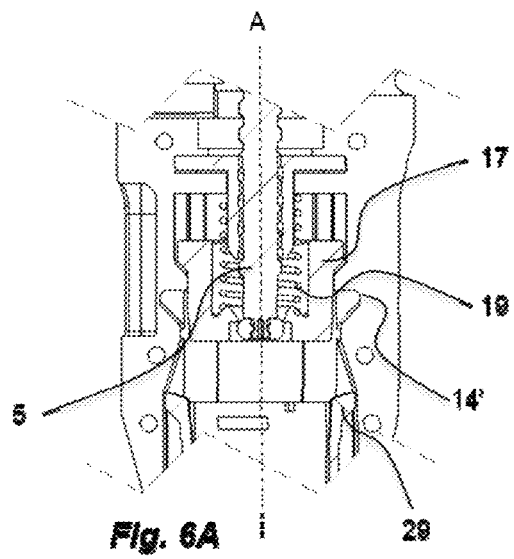
FIGS. 6A, 6B, 6C, 6D and 6E illustrate a cross-sectional views of all the sequences of the assembling the proximate and the distal parts of the injection device.
Figure 6B:
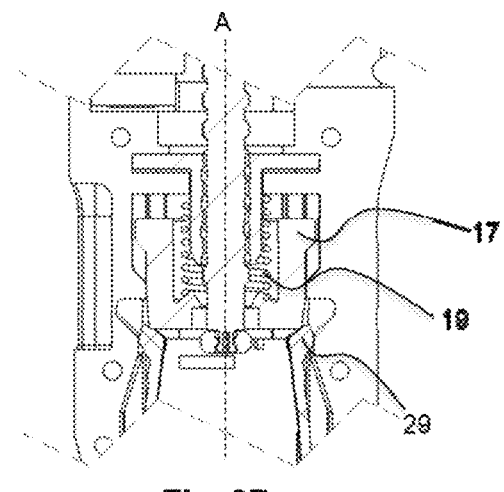
Figure 6C:
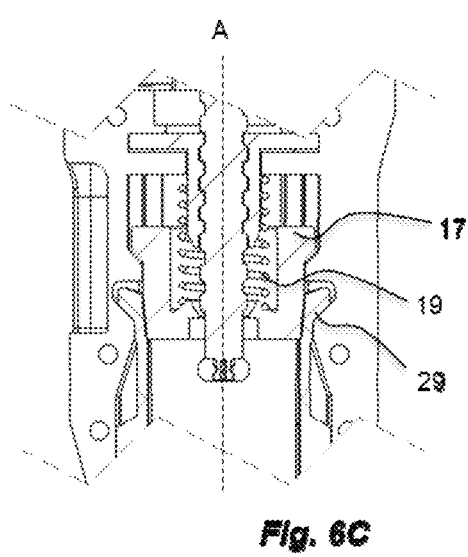

In a first connecting state of the medicament delivery device 10, at the very beginning of insertion by user' hand of the connecting end 23 of the unit 2 into the opening 16 of the unit 1 as in FIG. 6A, the flexible parts 25 are used to move the spring loaded locking element 17 axially. The flexible part 25 extension or ledges 29 is gliding without compression along the cylindrical surface 14. At the continued motion, the movement along the inclined surface 14A forces the flexible parts 25 flex radially inwardly as illustrated in FIG. 6B, pushing the locking element 17 towards the closed distal end 12 against the force of the spring 19. Being compressed inwardly, the flexible parts 25 are pushing away the locking element 17 which in its turn is compressing the locking spring 19 until the extensions 29 reach the groove 14'. The groove 14' accommodates the extensions 29 allowing them to flex outwardly as illustrated in FIG. 6C. This causes an increase in diameter of the opening 23' of the hollow connecting end 23 and thus releasing the locking element 17 from the pressure from the flexible parts 25. Now the locking element 17 is released and forced by the locking spring 19 to move towards the proximate unit 2 direction and enter this opening 23' (as illustrated in FIG. 6C) performing an outwardly directed pressure on the flexible parts or elements 25. The extensions or ledges 29 are locked into the groove 14' and do not allow the flexible part 25 to flex back inwardly relative to the axis A. This establish and lock the connection of the connecting ends 13 and 23 and the units 1 and 2 in one single movement automatically.

If desired to avoid any rotation between the units 1, 2, an anti-rotational ledge or an extension 21A (not shown) can be provided either as at least one circular ledge or preferably two ledges 21A on a part of the outer surface of the housing 21. Alternatively, the ledge 21A can be made as a longitudinal extension 21A on the outer surface of the housing 21. The ledge and/or extension 21A fits tightly in at least one corresponding recess 13A in the inner surface of the second connecting end 13 as illustrated in FIG. 6G, which is a cross-sectional view seen perpendicular to the axis A and illustrating two ledges/extensions 21A. This arrangement prevents any rotation of the unit 2 around the axis A relative to the unit 1.

It is preferred also to eliminate any gap between already interconnected units 1 and 2 which might naturally occur due to tolerances between the interacting parts such as the locking element 17 and the inner surface of the flexible parts 25 forming the opening 23'. The eliminated gap increases confidence among users when connecting the re-usable unit 1 to the disposable unit 2 signalling that the units 1, 2 are properly mounted. A tight fit between the units 1, 2 also increases the user's confidence in the robustness of the device 10 prior usage.

A gapless connection means that the inserted unit 2 shall be prevented from any movement in all degrees of freedom (e.g any translation or rotation relative the re-usable unit). To achieve this and still allow for deviations (e.g tolerances) during the manufacturing of the parts interacting in the connection of the two units 1, 2, the device 10 shall be able to eliminate all gaps due to the connection and still lock or unlock the units 1 and 2 relative each other.

Figure 6D:
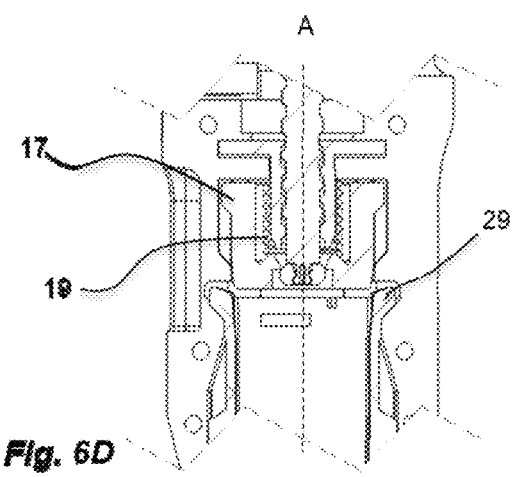
Figure 6E:
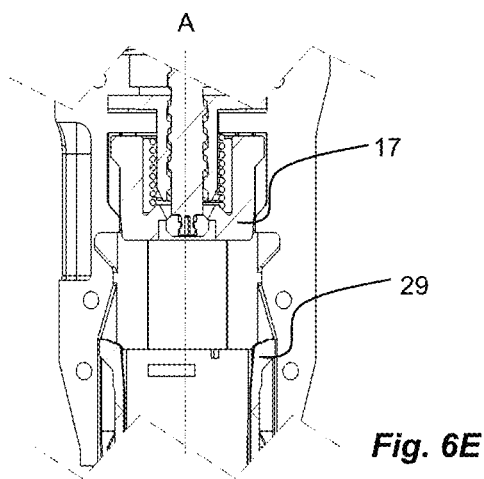
Figure 6G:
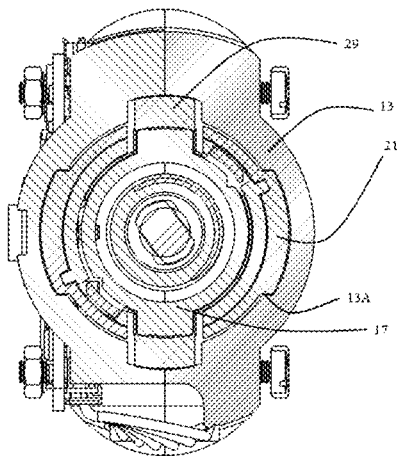
Figure 6F:
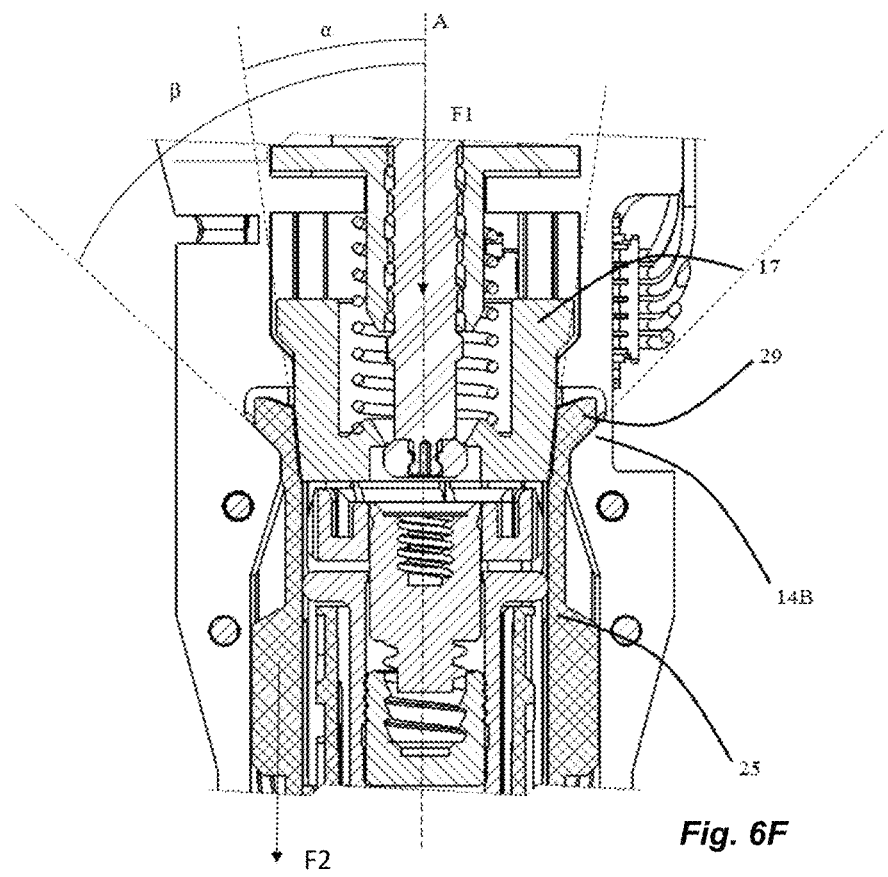
FIG. 6F clarifies the feature of a gap free locking mechanism for a tight connection eliminating the connection gap between the units; where

In this first embodiment, the gap elimination is achieved by using a first conical surface connection between the unit 1 connection end 13 (the surface 14B of the end 13 will be an inclined with an angle $\beta$ to the axis A) and the extension 29 of the flexible part 25 interacting with the surface 14B and having the corresponding inclination angle $\beta$; a second conical surface connection of the outer surface of the locking element 17, inclined with an angle $\alpha$ to the axis A, with the inner surface of the opening 23' of the connecting end 23 of the housing 21 as illustrated in FIG. 6F, having the corresponding inclination angle $\alpha$.

Figure 9A:
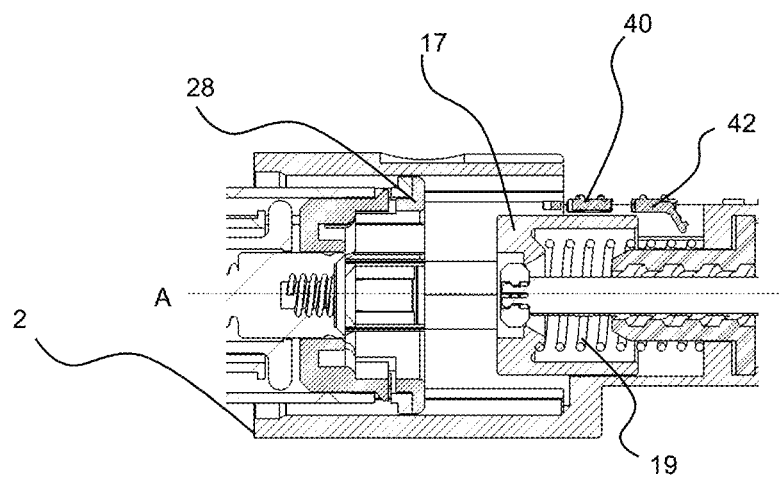
FIGS. 9A, 9B and 9C illustrate the cross-sectional views of insertion sequence and the sensors controlling the connection, injection and disassembling processes.
Figure 9B:
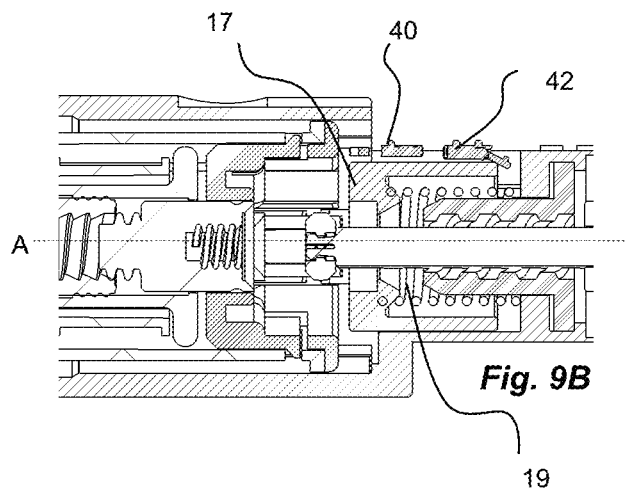
Figure 9C:
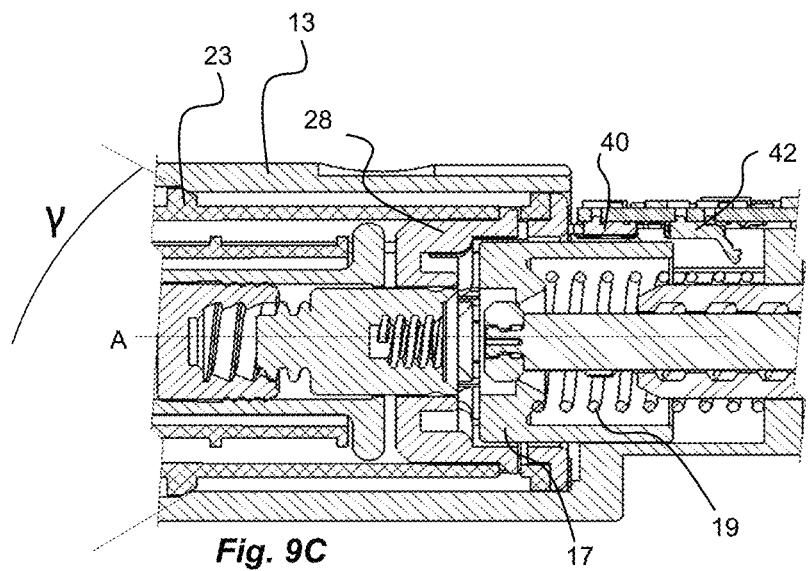

Additionally, a third conical surface connection between the connecting end 13 and the housing 21 at a distance in the proximate end direction along the axis A from the locking element 17, as illustrated in FIG. 9C, is arranged for longitudinal stabilisation of the connecting end 13 and the housing 21 relative each other and situated apart from the first and second conical surface type connections.

The third conical connection with an angle $\gamma$ between the connecting end 13 and the housing 21 and the axis A allows slightly vary the distance between these three connections longitudinally and therefore compensates for the tolerances when manufacturing the parts. All those conical surface connections allow a relative movement or adjustment of the interacting elements position relative each other in the axial direction so as to compensate for manufacturing dimensions' tolerances and provide a tight fit between the connected parts.

As shown in FIG. 6F, any force F2 applied in order to remove the unit 2 (e.i the plunger rod 5 force) will generate a radial force F3 (not shown) due to the angle of the flexible part 25 equal to the force F2 divided with a tangency of angle $\beta$. This force F3 will in turn generate a force component F4 in the axial direction A which is equal to force F2 multiplied with tangency of angle $\alpha$ divided with the tangency of angle $\beta$. The locking element 17 is pressed with the locking spring 19 force F1 and as long as the force F1 is greater than the resulting axial force F4 (not shown), the unit 2 will be locked and remained within the opening 16 of the unit 1. This means that in order to obtain a smaller, lighter and therefore weaker spring 19 for minimizing the effort required from the user for pushing against but which is still loading the locking element 17 with a sufficient force, the angle $0<\alpha<90°$ preferably shall be as small as possible, for example about 7-10°. For the same reason, the angle $0<\beta<90°$ shall be as big as possible, for example about 30-55°. The sufficient force is meant that this force F1 shall be enough to counteract the force F4 applied by the flexible parts 25 flexing inwardly and thus pushing out the locking element 17 towards the distal end. The conical type of the connections excluding the connection gaps might be advantageous between at least one of the locking element 17 and the flexible part 25 interacting surfaces, the flexible part 25 and/or their extensions 29 and the connecting end 13 of the unit 1 interacting surfaces and the connecting ends 13 and 23 of the units 1, 2.

To account for any tolerance errors on the parts as well as the position of the housing 21 of the disposable unit 2 called sometimes a cassette, the angle $\alpha$ is large enough to always ensure the tight fit within the flexible parts 25 for the locking element 17 and the unit 2 as well as a gap free connection between the flexible part 25 and the connecting end 13. Any deviations from a nominal dimension would result in a shorter or longer movement in the axial direction A for the locking element 17.

Varying tolerances could be of any types such as lengths, diameters or thickness of the parts. This conical type of the connections in addition to the simple anti-rotational ledge/ extension—recess connection keeps the two units 1, 2 locked relative each other in all degrees of freedom.

In a second device 10 state, after the injection is completed, when the medicament delivery device 10 is preferably to be easily disassembled, the driving unit 3 moves the plunger rod 5 axially towards the closed distal end 12 and therefore, the locking element 17, which is then connected to the plunger rod 5, follows in the same direction as illustrated in FIG. 6D exiting the opening 23'. This releases the inner surface of the flexible elements 25 from the pressure applied by the locking element 17 and thus allowing them to flex inwardly. The extensions 29 are able to leave the groove 14' due to flexing of the parts 25 inwardly and this enable a disconnection of the connecting ends 13 and 23 and the units 1 and 2 accordingly. The driving unit 3 via plunger rod 5 moves the locking element 17 in its initial resting position as illustrated in FIG. 6E.

Therefore, in the first connecting and locking state of the device 10, when the connecting end 23 is to be inserted into the opening 16, the ledge (29) is guided along the inclined surfaces 14A, 14B forcing the flexible part 25 to move radially and inwardly pressing by its outer edge the locking element 17 axially loaded by the spring 19 in the open end 13 direction until the ledge 29 reaches and is been accommodated by the groove 14', which allows the flexible part 25 move radially and outwardly relative to the axis A so as to snap lock the connecting end 23 relative to the connecting end 13 and thus the housing 11 relative the housing 21. Simultaneously expanded outwardly the flexible part 25 stops its pressure on the element 17 so as the spring 19 is released and forces the locking element 17 pushing it axially in the proximate housing 21 direction. The element 17 enters into the opening 23' on the connecting end 23 so as to press outwardly on the flexible part 25 when the flexible part 25 is interacting with the surfaces 14A, 14B of the opening 16 in the connecting end 13. This prevents disassembling of the connecting ends 13, 23 and thus, the housings 11, 21. In the second releasing state of the device 10 when the injection is already completed, the locking element 17 is axially moved by the driving element 5 in the distal closed end 12 direction. The flexible part 25 is being released from been pressured towards the connecting end 13 inner surfaces 14, 14A, 14B which allows the flexible part 25 move radially and inwardly towards the axis A and thus the disconnecting of the connecting ends 13, 23 and the corresponding housings 11, 21 relative each other.

As been explained above, the flexible part 25 is integrally arranged on the connecting end 23 of the proximate housing 21 which is to be inserted into a receiving opening 16 in the connecting end 13 of the distal housing 11. The receiving opening 16 is provided with a longitudinal cross-section shape of a various radial dimensions on its inner surface 14 and adapted to accommodate the flexible part 25 having a corresponding longitudinal cross-section on its outer surface, allowing in a first state of the device 10 an inserting and locking of the connecting ends 13, 23 of the units 1, 2 and their housings 11, 21 relative each other and in a second state of the device 10, releasing of the connecting end 23 of the unit 2 from to the connecting end 13 of the unit 1 thus releasing housings 11, 21 from connection to each other.

The flexible part 25 has an extending outwardly ledge 29 at its distal end is provided as an integral part of the housing 21. The housing 21 has the hollow connecting end 23 with an axial opening 23'. The connecting end 23 is adapted to be inserted into the receiving opening 16 of the connecting end 13 having inclined wall surfaces 14A, 14B and a groove 14' able to accommodate the ledge 29 for snap-locking the connecting ends 13, 23 relative each other and therefore the corresponding housings 11, 21.

FIG. 8 illustrates the connected units 1, 2 with the partly longitudinal cross-section of the distal unit 1 showing in a greater details in FIGS. 8A and 8B the frame 38 for mounting all elements and electronical sensors or detectors. In this embodiment the sensors are switches 40, 42 controlling the electrical motor 32. The switch 42 detects a movement of the locking element 17 and the switch 40 reacts on the insertion of the connecting end 23 of the proximate unit 2, sometimes called a cassette, by detecting the rear cup 28 of the connecting end 23 as illustrated in FIGS. 9A-9C.

FIGS. 9A-9C are the longitudinal cross-section views orthogonal to the cross-section as illustrated in Figured 8, 8A, 8B.

FIG. 9A shows a start of the insertion process, when the rear cup 28 of the insertion connecting end 23 of the unit 2 starts movement towards the distal closed end 12 of the unit 1 provided with the sensors 40, 42, forced by a user hand, and both sensors 40, 42 are still inactivated.

FIG. 9B illustrates a second position when the locking element 17 is forced towards the distal end of the distal unit 1 reaches the sensor 42 by its edge and activates it, while the sensor 40 is still inactivated as do not have a contact with the rear cup 28. FIG. 9C illustrates a third position, where the rear cup 28 reaches and activates the sensor 40 while the sensor 40 is became released and inactivated as the locking element 17 is moved into the opening 23' in the connecting end 23 (by the spring 19) so as to secure the units 1 and 2 interconnection. If the sensor 42 is not released, it indicates that the units 1 and 2 are not properly connected. Those sensors 40, 42 signal the correct automatic connecting sequence.

Figures 10A, 10B:
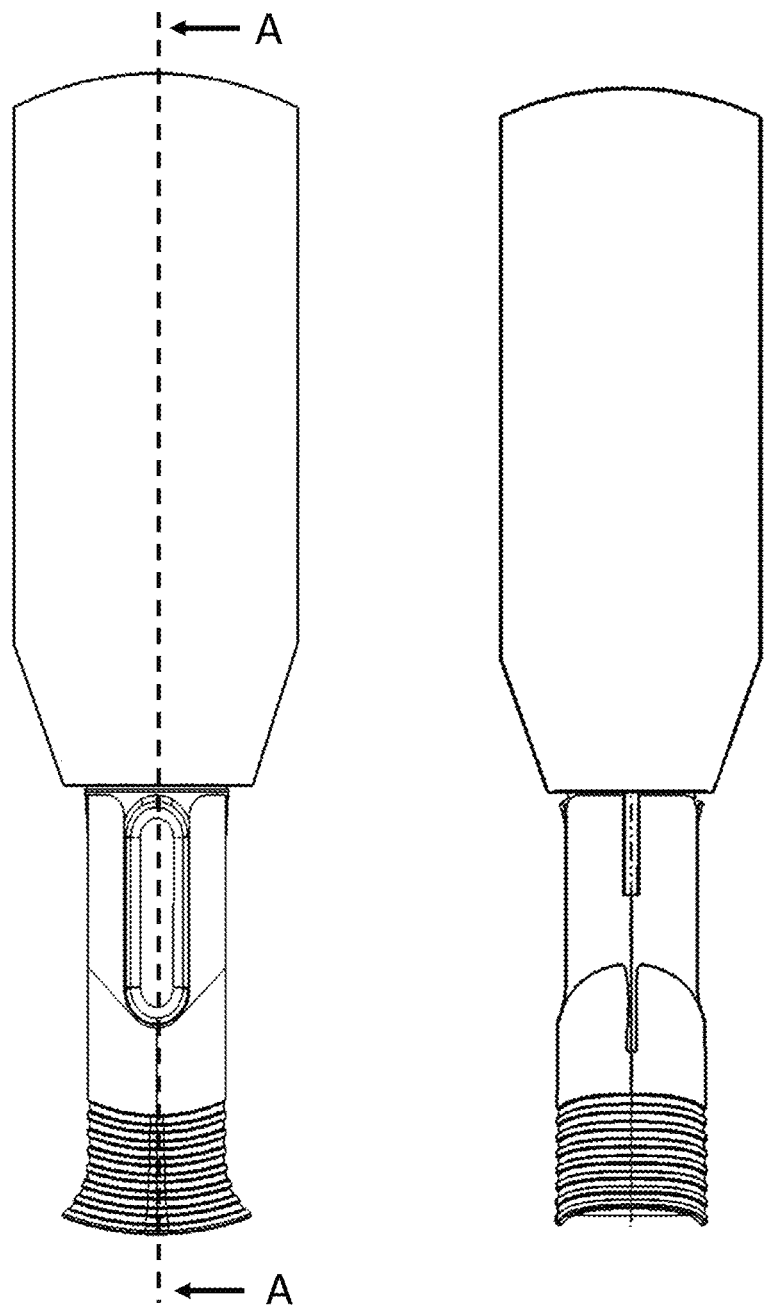
FIGS. 10A and 10B illustrate two side views of a second embodiment of the medicament delivery device according to the invention.
Figure 14:
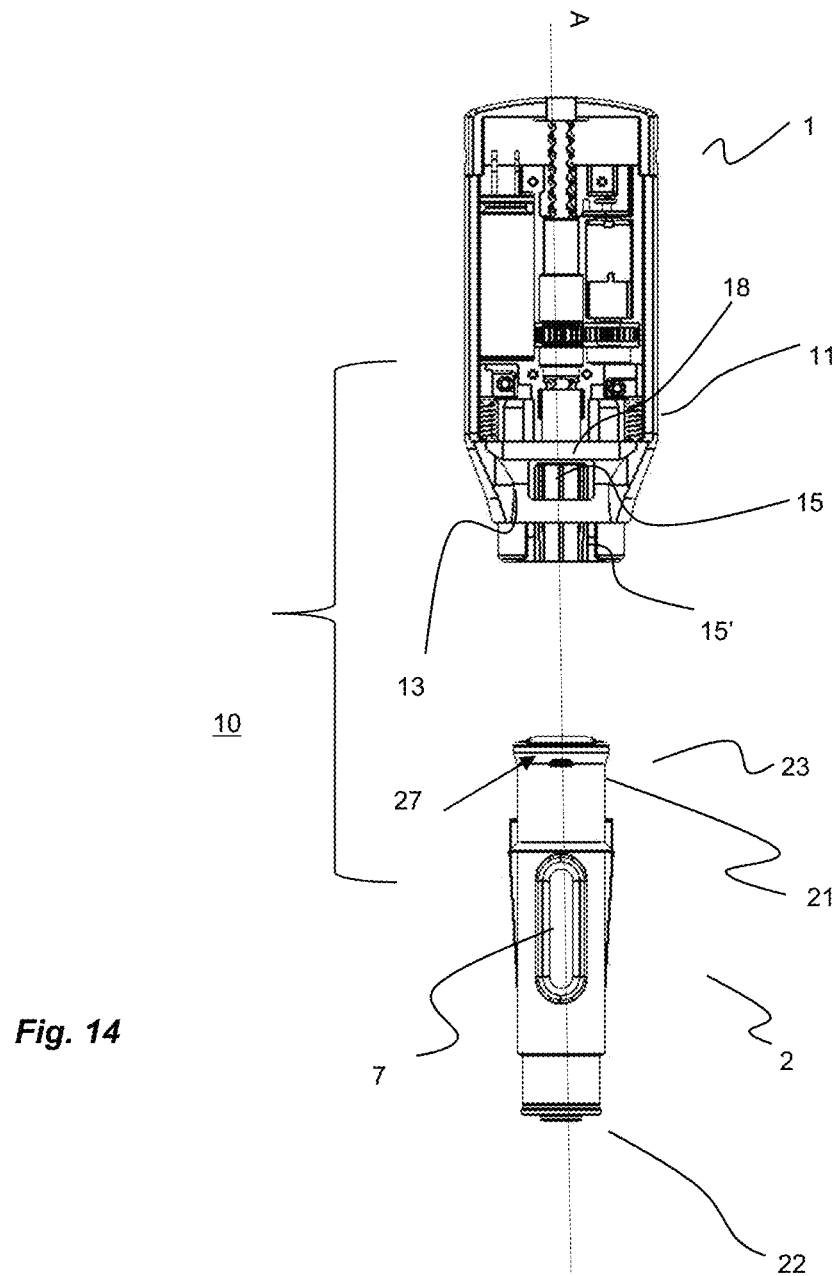
FIG. 14 illustrates a cross-sectional view of the second embodiment with two separate reusable and disposable units forming together the medicine delivery device.

FIGS. 10A, 10B illustrate two side views of an assembled device 10 of a second embodiment of the invention and FIG. 14 shows two separate coaxial units 1 and 2, with a longitudinal cross-section of the distal reusable unit 1 to be joined along the axis A. The proximate disposable unit 2 comprises a housing 21, a proximal end 22 for medicament delivery and a distal end 23 for connection to the proximal reusable unit 1. The hollow housing 21 has a monitoring window 7 and includes a medicament container 4 (not shown here).

Figure 11:
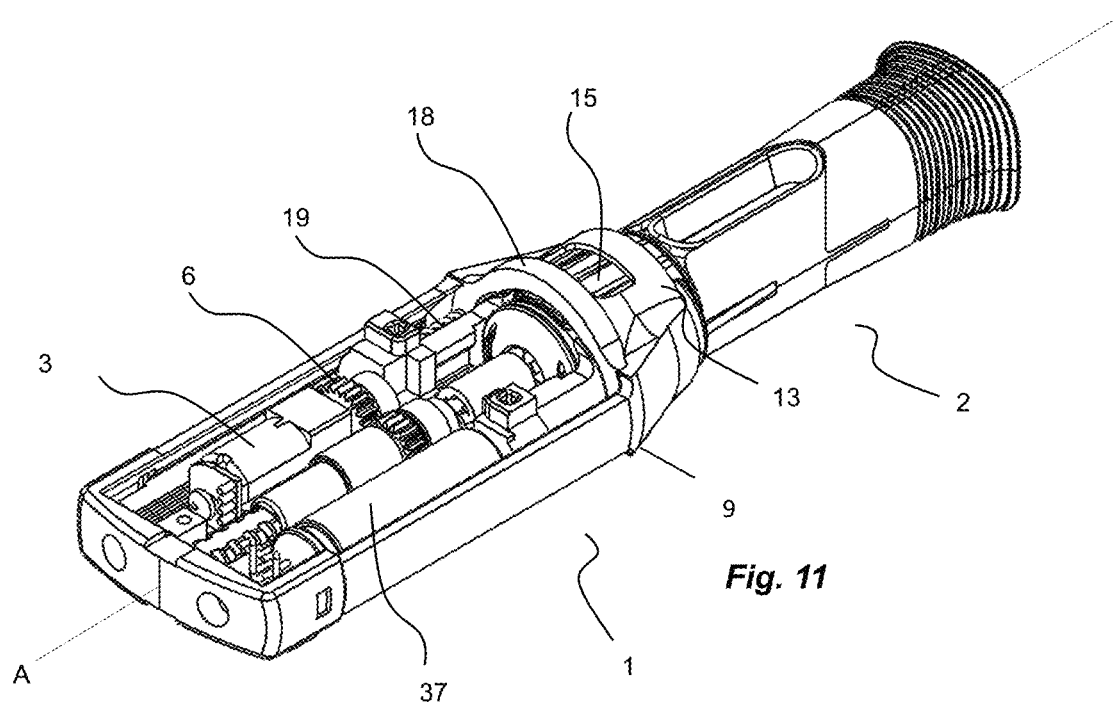
FIG. 11 illustrates an isometric view of the second embodiment with a partly removed housing of the reusable unit.
Figure 12:
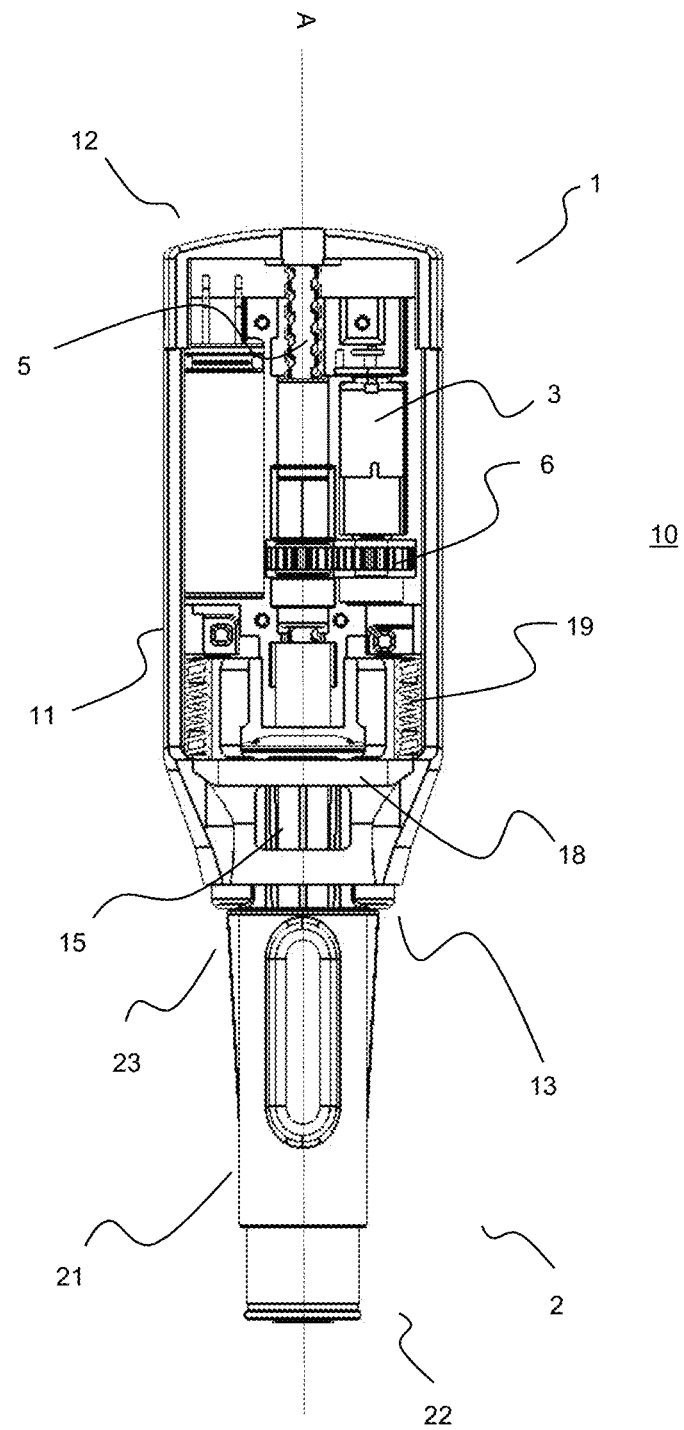
FIG. 12 illustrates a partly cross-sectional view of the medicament delivery device with the connected the first and the second units.

In FIG. 11 illustrating the second embodiment, a part of the housing 11 is removed for an illustration purpose. The proximate disposable unit 2 is inserted into the distal reusable unit 1 of the medicament delivery device 10. A drive unit 3 provided with a transmission 6 and a battery 37 are mounted on a frame 38 (not visible) adjacent to the closed end 12 of the unit 1. The stationary frame 38 (FIG. 16B) is connected to the housing 11 which is illustrated in FIG. 12. An inner element 9 in form of a movable frame 9 is arranged to move reciprocatingly within the housing 11 by the driving unit 3 via the driving element 5. The frame 9 is axially loaded by a couple of springs 19, for example the spiral springs 19, situated between the stationary frame 38 and the movable frame 9. A locking element 18 is integrated with the movable frame 9 forming by its proximate end a second proximate connecting end of the unit 1.

In the second embodiment, the plunger rod 5 or the driving element 5 is reciprocatingly movable by the driving unit 3 via a transmission 6 so as to interact with the medicament container 4. The medicament container 4 might be one of the syringe S and the cartridge C for performing an injection: At the same time, the plunger rod 5 is also used for locking the snap connection of the connecting ends 13, 23 of the units 1, 2 of the medicament delivery device 10 by the locking element 18 and releasing the connecting ends 13, 23 and the units 1, 2, housings 11, 21 connection after the injection is completed.

As more detailed illustrated in FIG. 11, the connecting end 13 of the distal reusable unit 1 is formed by at least one, but preferably by at least two flexible parts 15 extending axially in the distal closed end 12 direction and defining a receiving opening 16 for insertion of the connecting end 23 of proximate disposable unit 2. At least one the flexible part 15 is integrally arranged on the stationary frame 38 which carries also the driving unit 3. The flexible part 15 extends in the axial direction towards the distal closed end 12 and forming a receiving opening 16. The open connecting end 13 is integrated with the locking element 18 surrounding the flexible part 15 and is axially movable by driving unit (3) via the driving element (5) relative the stationary housing (11) allowing a first inserting and locking state of the connecting ends (13, 23) and a second release state of the connecting ends (13, 23) relative each other.

The flexible part 15 has a wedge-shaped guiding extensions 15' on its outer surface interacting with an inner surface 18' of the locking element 18. The connecting end 23 of the housing 21 has a longitudinal cross-section shape of the different dimensions and a ledge 29 is formed at the end of its outer surface 24.

The flexible parts 15 are connected to the stationary frame 38.

The plunger rod 5 is arranged to activate the syringe S or the cartridge C for performing the medicament injection when moved axially towards the disposal part 2.

According to the invention, it also serves for disconnecting of the units 1 and 2, when the injection is completed and the disposable unit 2 is to be removed.

Figure 13:
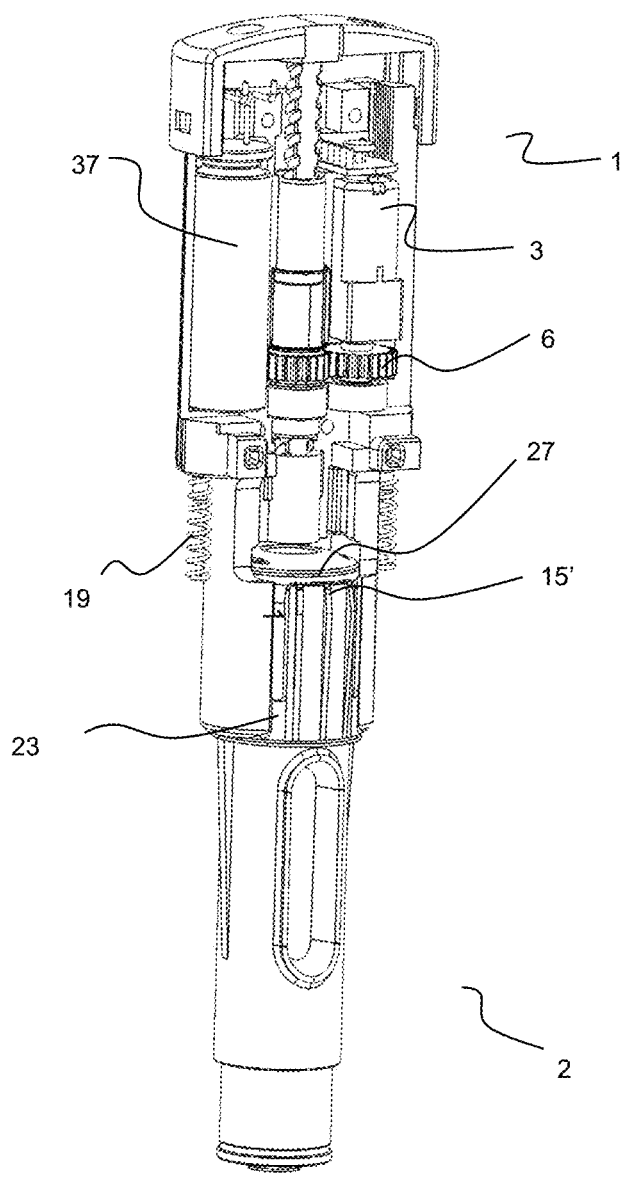
FIG. 13 illustrates an isometric view of the medicament delivery device according to the second embodiment with a removed housing of the reusable unit and the locking element integrated with it.

While the connecting end 23 in all embodiments of the invention might be of any cross-sectional shape (round, oval, triangular, polygonal etc) seen perpendicularly to the longitudinal axis A, in this particular embodiment, the connecting end 23 has preferably a cylindrical shape with a conical circular extension or ledge 27 at its distal end as illustrated in FIGS. 13 and 14. FIGS. 11 and 12 show that the flexible elements 15 are situated inside the movable frame 9 which is integrated with the locking element 18—The locking element 18 surrounds the flexible elements 15 for interaction with their outer surface.

Figure 15:
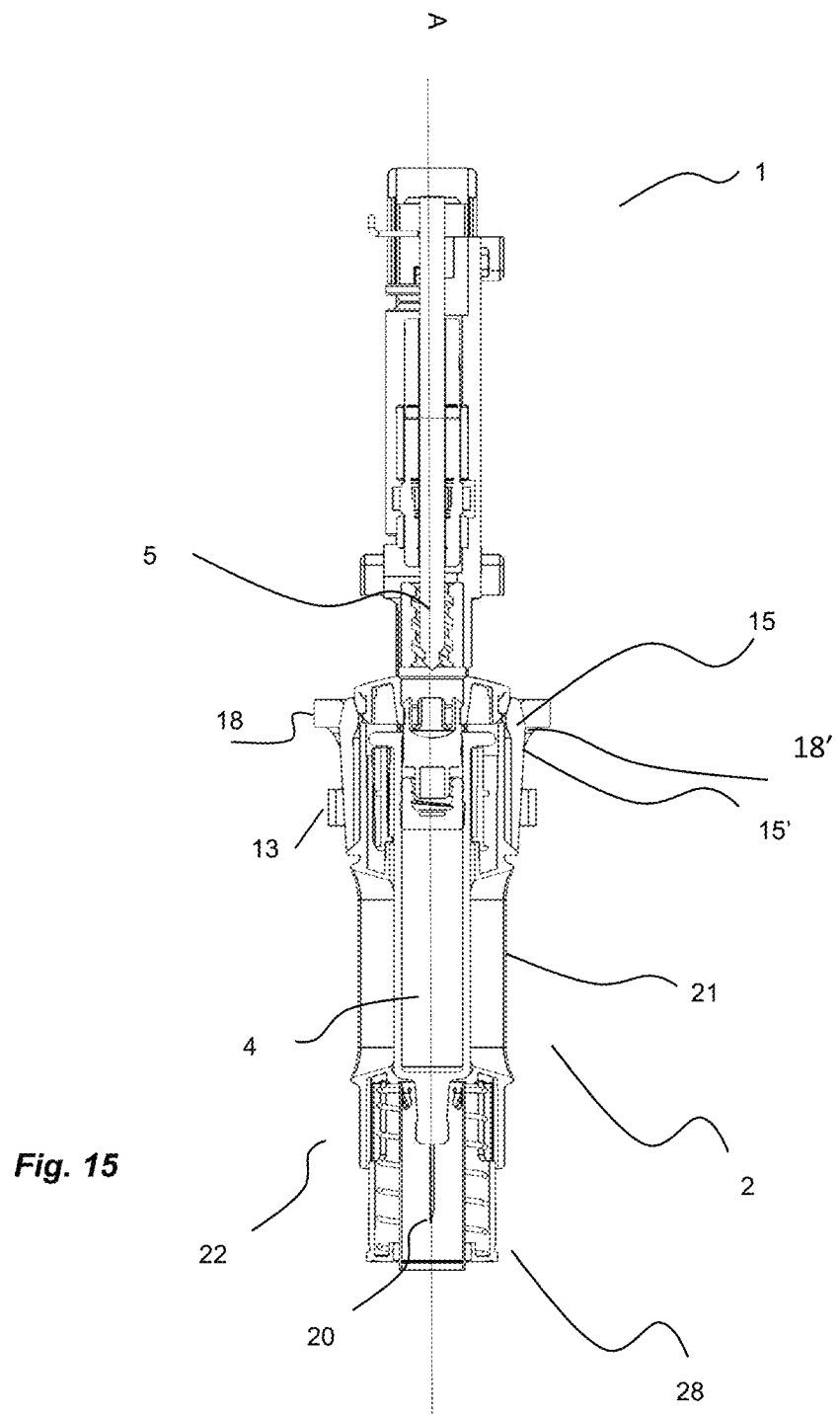
FIG. 15 illustrates a still another cross-sectional view orthogonal to the cross-section of FIG. 14, with the connected units according to the second embodiment.

The flexible elements 15 on their outer surfaces are provided with longitudinal wedge-shaped extensions 15' that extend in the axial direction A. In this second embodiment as illustrated in FIG. 13, the wedge-shaped extensions 15' have varying height with increasing and decreasing parts. These wedge-shaped extensions 15' interact with the inner surface 18' of the circular locking element 18 as shown in FIG. 15. When the connection end 23 is inserted into the receiving opening 16 formed by the flexible elements 15, the distal ends of the flexible elements 15 in the axial direction are resting on the conical extension 27 of connecting end 23 and work as a stop for a snap connection.

FIG. 15 is an orthogonal cross-section view along the arrows A in FIG. 10A, illustrating the connected units 1, 2 of the device 10; the proximate end 22 of the unit 2 for the medicament delivery is provided with a protecting cup 28 covering an injection needle 20 of the medicament container 4. A plunger rod 5 is connected by one end to the closed distal end 12 and the other opposite plunger rod 5 end is adapted to push a plunger 41 (shown in FIG. 1) of the container 4 activating a medicament delivery. The plunger 5 is arranged to move the frame 9 against the force applied by the spiral springs 19 towards the proximate end of the unit 1. This movement releases the connection of the inner surface 18' of the locking circular element 18 and surrounded wedge-shaped extensions 15' of the flexible elements 15, allows the elements 15 flexing outwardly increasing a diameter of the receiving opening 16 and thus enables dissembling of the units 1 and 2 as the circular extension 27 is able to pass though.

Figure 16A:
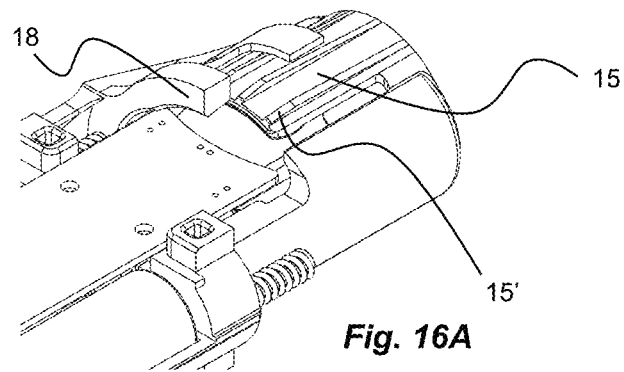
FIG. 16 illustrates a sequence of the insertion process of the disposable unit into the reusable unit.
Figure 16B:
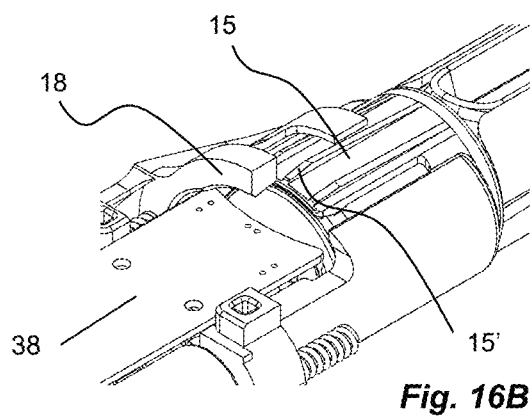
Figure 16C:
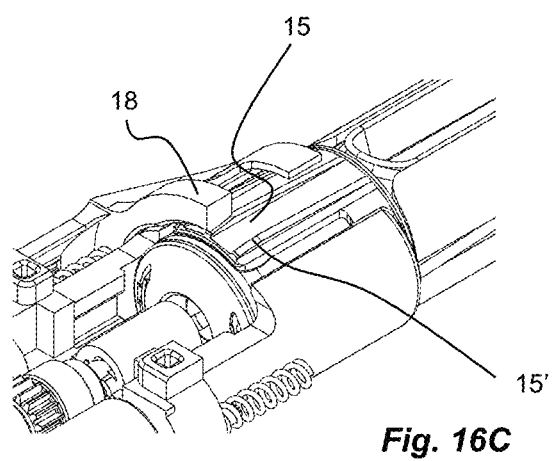
Figure 17:
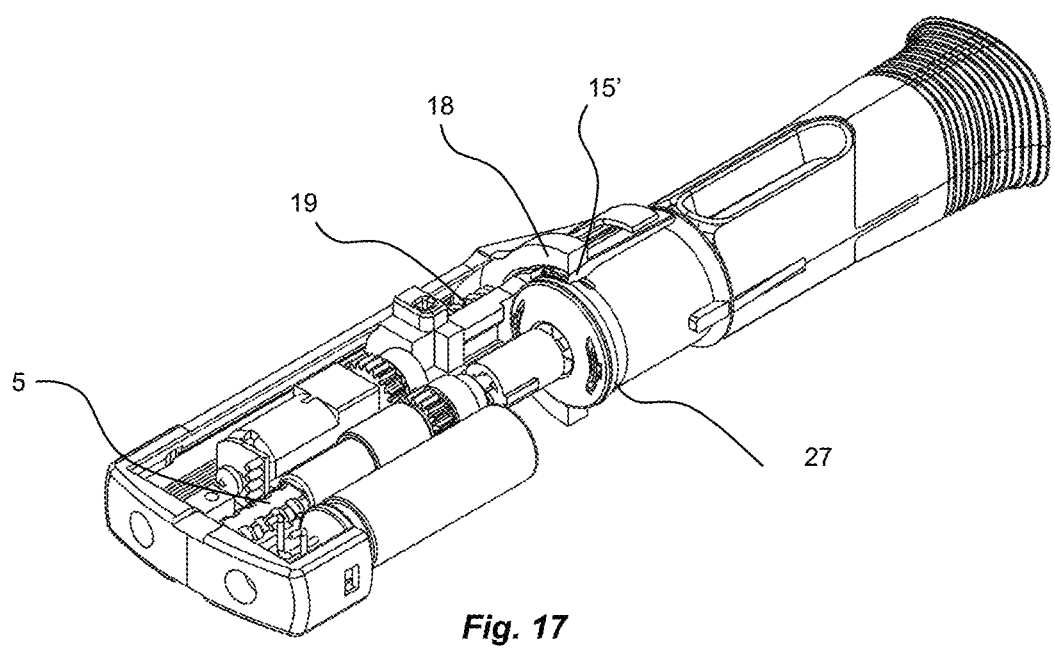
FIG. 17 illustrates the connected reusable and disposable units of the device according to the second embodiment with a partly removed housing of the reusable unit.

FIGS. 16A-C illustrate this process in the greater details. FIG. 16A shows only a hollow connecting end 13 of the unit 1 with the flexible parts 15 forming a receiving opening 16 for insertion of the connecting end 23. FIG. 16B shows a process of an insertion of the connecting end 23 with a monitoring window into the opening 16 of the connecting end 13. The driving element 5 moves the frame 9 with integrated locking element 18 relative to the stationary frame 38 with the integrated flexible parts 15 in a distal close end 12 direction. The geometry of the connecting end 13 and the locking element 18 is such that allows a radial movement of the flexible parts 15 outwards, The flexible parts 15 in this stage are forced to flex outwardly relative to the axis so as to allow passage of the circular extension 27 of the bigger diameter than the connecting end 23 through the opening 16 when the unit 2 is being inserted in the unit 1 until the ends of the flexible parts 15 will rest on the circular extension 27. Then, the driving element 5 moves the frame 9 with the locking element 18 in the distal closed end 12 direction so as to bring the extensions 15' on the outer surface of the flexible parts 15 in a contact with the inner surface 18' of the locking element 18 that is illustrated in FIG. 16C. This is a locked position of the device 10 as the locking element 18 prevents the flexible parts 15 to move radially and outwardly thus locking the snap-connection of the units 1 and 2.

The drive unit 3 such as an electrical motor 32 in this second embodiment is equipped with a battery 37, provided with the control sensors (not shown) and performs the plunger rod 5 reciprocal movement, but the other types of driving units might be used.

The flexible part 15 has a wedge-shaped guiding extensions 15' on its outer surface interacting with an inner surface 18' of the locking element 18. A connecting end 23 of the housing 21 has a longitudinal cross-section shape of the different dimensions and a ledge 27 is formed at the end of on its outer surface 24.

In the first insertion and locking state of the device 10, the connecting end 13 with the locking element 18 is axially movable by the drive unit 3 via the driving element 5 in direction to the distal closed end 12 allowing radially and outwardly movement of the flexible part 15 relative to the axis A. This is releasing the wedge-shaped extensions 15' of the flexible element 15 from interacting with the inner surface 18' of the locking element 18 thus increasing diameter of the receiving opening 16 diameter. This allows the insertion of the second connection end 23 with the ledge or circular extension 27 of the larger diameter into the receiving opening 16 and the snap locking. The motor or electrical driving device 32 moves the movable frame 9 via the driving element such as a plunger rod 5 relative to the stationary frame 38. The springs (19) are situated between the movable connecting end 13 and the stationary frame 38 connected to the housing (11) and compressed and released by the drive unit 3. The drive unit 3 is controlled by the sensors 40, 42 so as to react on the insertion of the connecting end 23 allowing the movement of the connecting end 13 by the springs 19 in the opposite to the closed end 12 direction so as to perform the snap locking and maintaining of the ends 13, 23 relative each other. When the connecting end 23 is inserted and the circular extension 27 has passed the distal edge of the flexible parts 15, a typical snap-connection "click" sound is produced informing the user that the connection is established.

In the second state of the device 10, after completing an injection, the drive unit 3 is controlled to react by moving the connecting end 13 in direction of the closed end 12, thus releasing the wedge-shaped extensions 15' from interacting with the inner surface 18' of the locking element 18 from the locked state and allowing the flexible part (15) to flex outwardly relative to the axis A, thus releasing the connecting ends 13, 23 of the units 1, 2 from connection with each other.

Then, when the motor 32 senses this via sensors 40, 42 that the injection is completed, it moves the plunger rod 5 in the proximate closed end 12 direction, and the previously compressed springs 19 are released and force the movable frame 9 with the locking element 18 move to the proximate unit 2 direction, releasing the connection of the wedge-shaped extensions 15' and the inner surface 18' of the locking element 18 so as allow the flexible elements 15 to flex outwardly relative to the axis A allowing a passage of the ledge 27 and thus release the connecting end 23 of the unit 2 from the connecting end 13 of the unit 1.

The axial reciprocating movement of the one of the flexible part 15 and the locking element 18 is achieved due to interaction of the plunger rod 5 and the spring 19 axially loading the locking element 18.

Figures 18A, 18B:
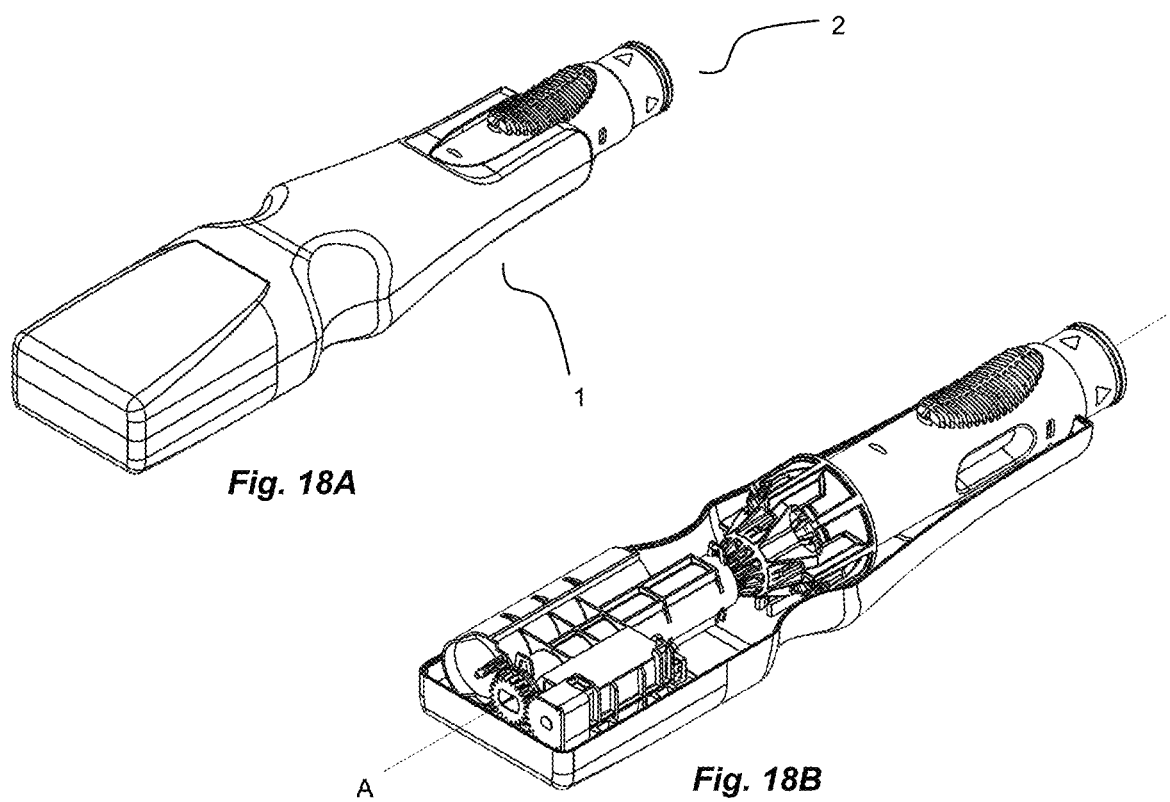
FIG. 18A illustrates an isometric view of the medicament delivery device according to the third embodiment.
FIG. 18B illustrates the same device with a removed upper half of the housing of the reusable part or unit.
Figure 19:
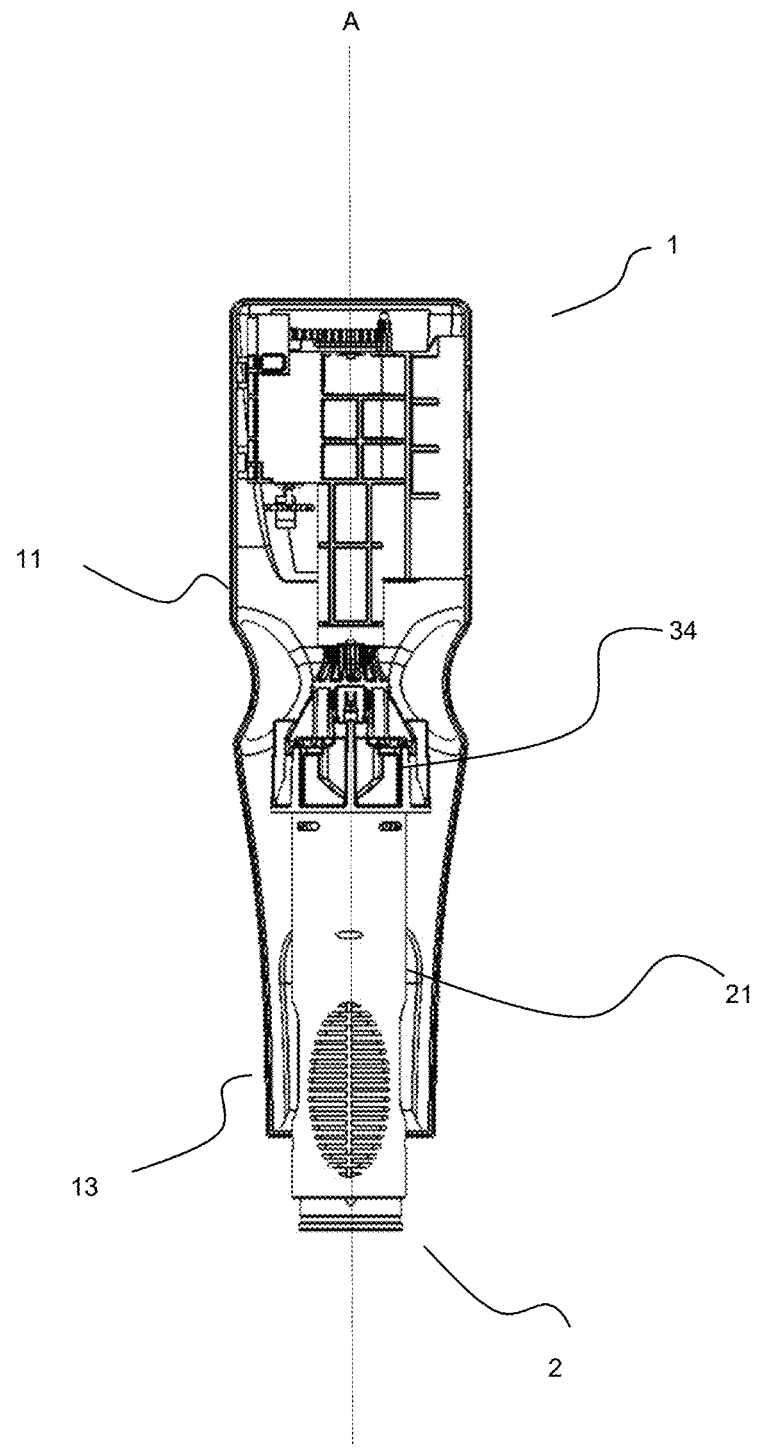
FIG. 19 illustrates a cross-sectional view of the interconnected parts of the medicament delivery device according to the third embodiment.

According to a third embodiment of the invention which is illustrated in FIG. 18A, 18B, a medicament delivery device 10 has a re-usable distal unit 1 with a housing 11 that is partly removed in FIG. 18B and a disposable unit 2 having a housing 21 containing a medicament container. A separate holder 34 as illustrated in FIG. 19 is inserted into the housing 11 and forms a receiving opening 16.

Figure 20:
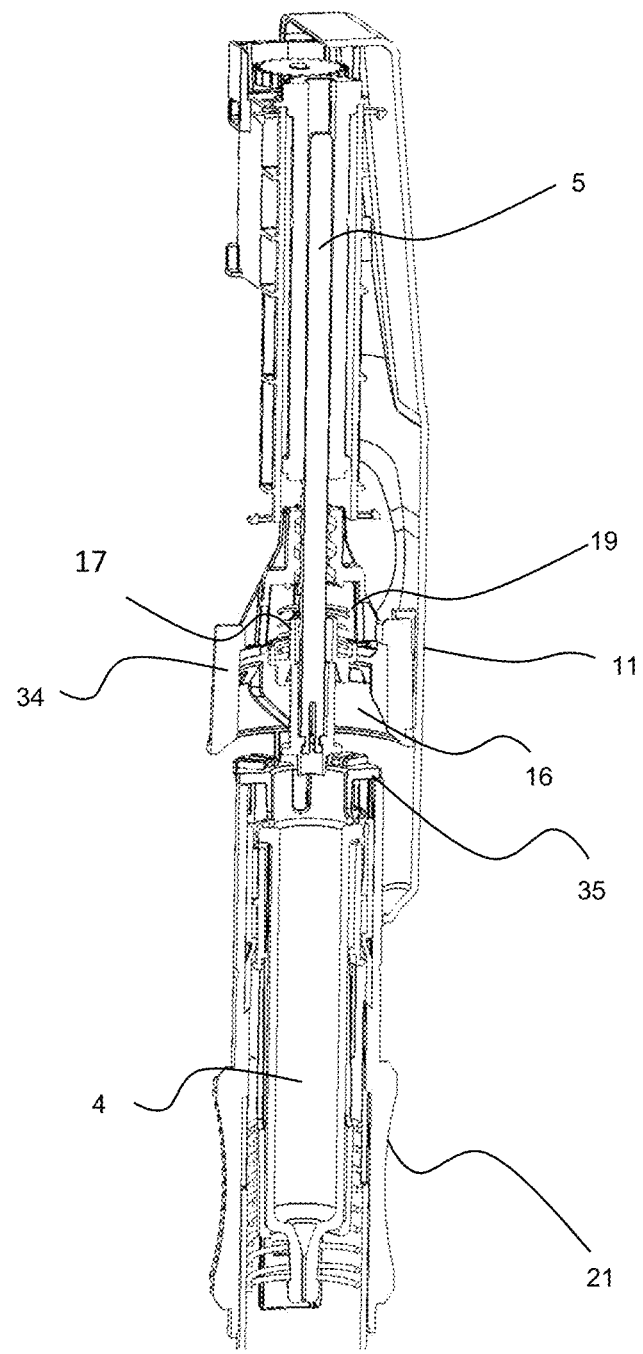
FIG. 20 illustrates a cross-sectional view, orthogonal to the view as shown in FIG. 19, of the device according to the third embodiment of the medicament delivery device.
Figure 22A:
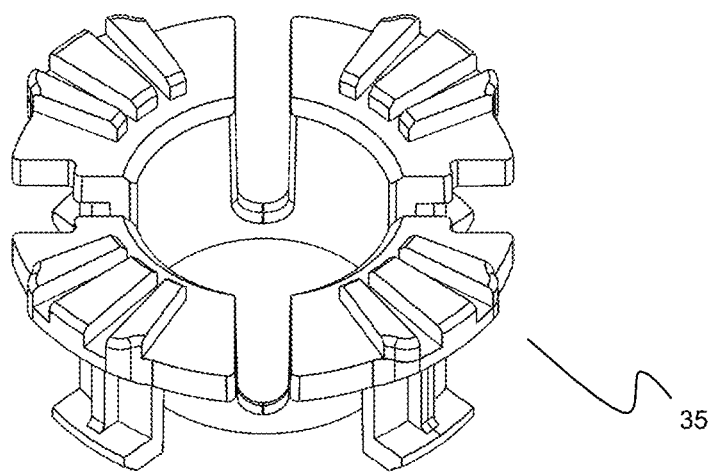
FIGS. 22A and 22B illustrate an isometric view of a separate flexible part or element used in the third embodiment of the medicament delivery device according to the third embodiment of the invention.
Figure 22B:
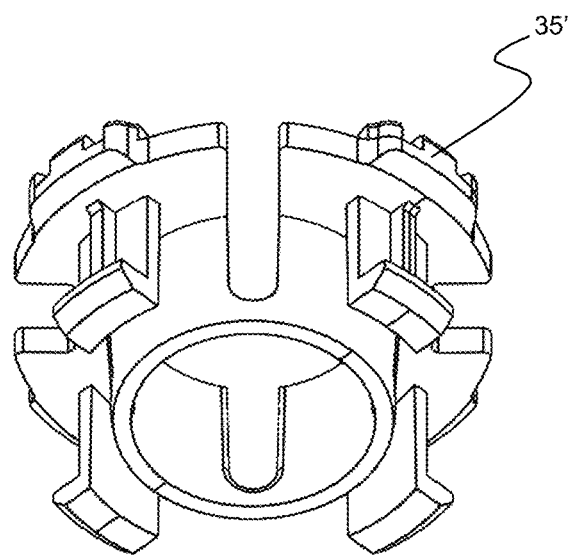

The housing 21 of the disposable part 2 containing a syringe 4 as illustrated in FIG. 20, the housing 21 is to be inserted into the housing 11 of the re-usable distal unit 1. A separate flexible element or part 35 is arranged on a flange end surface of the housing 21 in the third embodiment of the invention. A separate locking element 17 is provided between the holder 34 and the flexible part 35 and loaded axially by a spring 19 in direction of the proximate unit 2 as can be seen in FIG. 20. The flexible part 35 has a circular ledges 35'.

The flexible part 35 has at least two outwardly extending ledged 35' for interaction with at least two slits 34' into the holder 34. In the first inserting and locking state of the device 10, the connecting end 23 of the housing 21 is inserted into the holder 34 of housing 11. The flexible part 35 is forced along the guiding surface 34A, 34B of the opening 16 in the holder 34 axially towards the closed end 12 of the housing 11 against the spring 19 which is loading the locking element 17 axially in the open end 13 direction, when the ledges 35' are accommodated by the slits 34' providing the snap-connection of the connecting ends 13, 23 due to flexing outwards relative to the axis A. The movable locking element 17 is moved axially by the spring 19 in the direction of the open end 13 preventing the extending ledged 35' movement radially and inwardly relative to the axis A and thus locking the connecting ends 13, 23 relative each other. In the second disconnecting state of the units 1 and 2 of the device 10, the locking element 17 is moved axially by the driving element 5 in the direction of the distal closed end 12 of the housing 11 so as to release the flexible part 35 and allow the ledges 35' move radially and inwardly relative to the axis A allowing the disconnection of the connecting ends 13, 23 and thus the housings 11, 21. The locking element 17 in the third embodiment can be made as a locking ring 17

The flexible part 35 is made as a separate element 35 with at least two ledges 35' and arranged on the connecting end 23. The receiving opening 16 in the connecting end 13 is provided in the holder 34 which is inserted into the housing 11 of the connecting end 13 as a separate element. The locking ring 17 is inserted into the connecting end 13 of the housing 11 and interacts with the flexible element 35. The opening 16 is formed in the holder 34 and has an inner surface adapted to guide and accommodate the flexible part 35 and allowing an inserting and locking the connecting end 23 relative to the connecting end 13 in a first state of the device 10 and in a second state of the device 10 allows a releasing of the connecting end 23 of the unit 2 relative to the connecting end 13 of the unit 1.

Figure 23A:
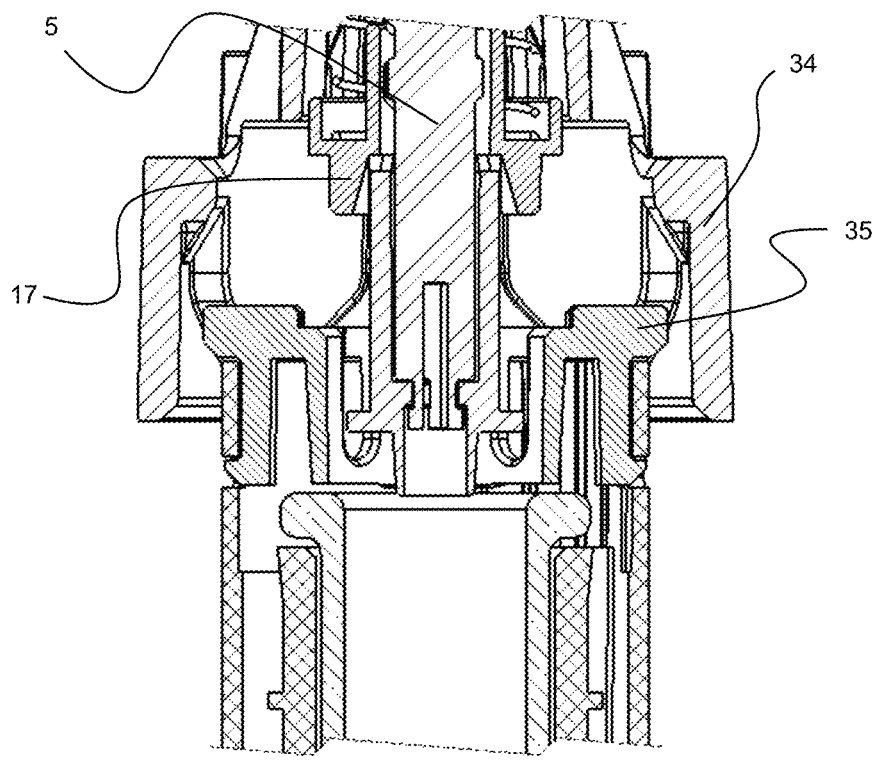
FIGS. 23A, 23B and 23C illustrate all sequences of connection of the two reusable and disposable parts or units of the medicament delivery device according to the third embodiment of the invention.
Figure 23B:
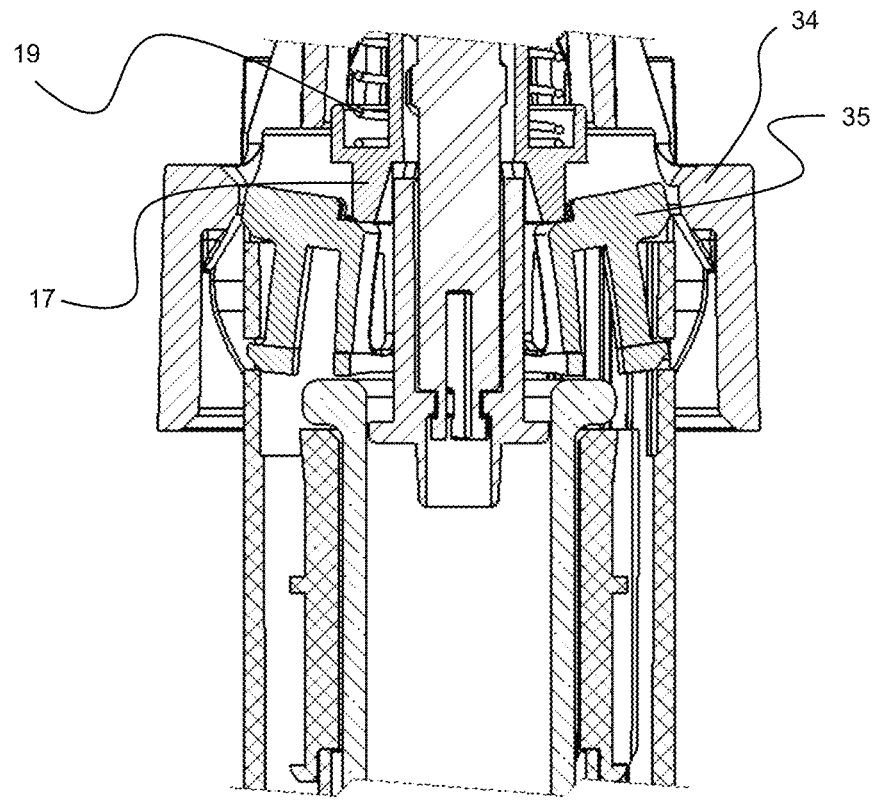
Figure 23C:
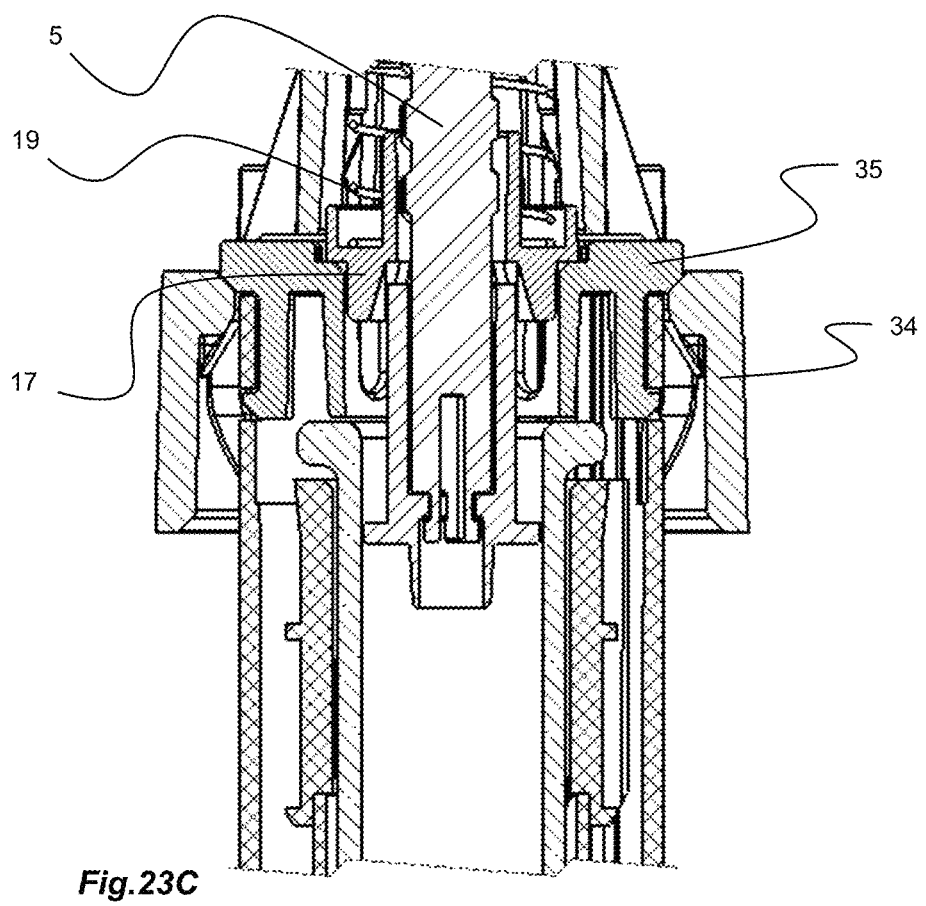

FIGS. 23A-23C depict a sequence of the connection and disconnection of the automatic medicament delivery device 10 of the third embodiment. FIG. 23A illustrates initial stage of the insertion when the unit 2 is pushed by hand into the unit 1, The guiding profiled surfaces 34A, 34B on the inner surface of the holder 34 as illustrated in FIG. 21B force the flexible part 35 ledges 35' into the corresponding slits 34' in a first connected state. FIG. 21A illustrates the separate holder 34 according to the third embodiment of the invention receiving a separate flexible part 35. FIG. 23B illustrates that the flexible part 35 is been deformed due to its ledges 35' are guided into the slits 34'. Forced by the spring 19, the locking element 17 will be moved towards the proximate unit 2 entering the inner opening into the flexible element 35 and pressing outwards its fixing the ledges 35' into the slits 34'. Therefore, the device 10 is in the first connected and locked state, and an occasional disengagement of the units 1 and 2 is prevented.

All important components are made of plastic by a precision moulding except for the driving unit 3, battery and springs. The container 4 can be made from one of a glass and a plastic material. The plastic material can be made transparent to allow monitoring of the injection process or none-transparent coloured.

FIG. 23A illustrates a connection of the units 1 and 2 process, when the housing 21 of the unit 2 is to be inserted into the receiving opening 16 in the holder 34 of the unit 1. The holder 34 has on its inner cylindrical surface a number of slits 34' corresponding a number of the circular ledges 35' and accommodating the flexible part 35 circular ledges 35' when the part 35 is forced by the axially moved housing 21 into the holder 34 opening 16.

FIG. 23B shows that during insertion by the user hand, the guiding surface of the holder 34 presses inwardly the flexible element 35 ledges 35'. The flexible element 35 in its turn pushes the licking element 17 axially in the distal closed end 12 direction. Then the ledges 35' reach and accommodated by the slits 34', the ledges 35 are flexed outwardly releasing the contact with the locking element 17.

The axially movable locking element 17 is loaded by the spring 19 in the direction to the proximate disposal unit 2 direction and is movable into the axial opening into the flexible part 35 so as to press outwards its ledges 35' accommodated by the holder slits 34'. Then a typical snap-connection sound "click" is heard and the connection is firmly ensured. The locking element 17 in this position does not allow the flexible part 35 circular ledges 35' movement inwardly towards the axis A so as to release the snap-connection between the housings 11 and 21 of the re-usable 1 and the disposable 2 parts.

FIG. 23C illustrates the position, when the injection process is completed, the plunger rod 5 is moved axially to the distal closed end 12 of the re-usable distal unit 1 by the driving unit 3. As the locking element 17 is connected to the plunger rod 5, it is removed from the engagement with the flexible part 35. Then the flexible part 35 ledges 35' are allowed to flex inwardly towards the axis A and disengage with the slits 34' of the holder 34 thus releasing the units 1 and 2 snap-connection.

The flexible part 35 has at least two outwardly extending ledged 35' for interaction with at least two slits 34' into the holder 34. In the first inserting and locking state of the device 10, the connecting end 23 of the housing 21 is inserted into the holder 34 of housing 11 and forced the flexible part 35 along the guiding surface 34A, 34B of the opening 16 in the holder 34 axially towards the closed end 12 of the housing 11 against the spring 19 which is loading the locking element 17 axially in the open end 13 direction. When the ledges 35' are accommodated by the slits 34' providing the snap-connection of the connecting ends 13, 23 due to flexing outwards relative to the axis A. The movable locking element 17 is moved axially by the spring 19 in the direction of the open end 13 preventing the extending ledged 35' movement radially and inwardly relative to the axis A and thus locking the connecting ends 13, 23 and the housings 11, 1 relative each other. In the second disconnecting state of the device 10, the locking element 17 is moved axially by the driving element 5 in the direction of the distal closed end 12 of the housing 11 releasing the flexible part 35 and allowing the ledges 35' move radially and inwardly relative to the axis A allowing the disconnection of the connecting ends 13, 23 and thus, the units 1 and 2 and their housings 11, 21.

In all embodiments within the scope of the invention, the housings 11, 21 of the first 1 and second 2 units might have one of a circular, oval and polyhedron cross-section shape.

The housings 11, 21 of the first 1 and second 2 units might have the same cross-section shapes.

The housings 11, 21 of the first 1 and second 2 units might have the same outer dimensions.

While the invention has been illustrated and described in detail in the drawings and foregoing description, it is to be understood that the illustration and the description are to be considered as exemplary and not as limiting. It is to be understood that any changes and or modifications may be made by those of ordinary skills within the scope of the following claims.

The invention claimed is:

1. A medicament delivery device having an axis A, the device comprising:
a first unit having a distal closed end and an open connecting proximate end, the open connecting proximate end comprising a driving unit with a driving element that moves in a reciprocating fashion; and
a second unit with a housing adapted to receive a medicament container and having a first proximal medicament delivery end and a second distal connecting end, where the second distal connecting end is adapted to be connected with the open proximate connecting end of the first unit by insertion of the second connecting end into the open connecting proximate end along the axis A,
wherein one of the open connecting proximate end and second distal connecting end is equipped with at least one flexible part that moves radially inwards and outwards relative to the axis A due to a force created by the insertion of the second distal connecting end into the open connecting proximate end,
wherein a movable locking element is arranged coaxially within the first unit,
wherein the movable locking element is configured to interact with the at least one flexible part due to a relative axial movement of the at least one flexible part and the locking element so as to lock the open connecting proximate end and the second distal connecting end of the device relative to each other,
wherein the at least one flexible part has a wedge-shaped guiding extensions on its outer surface interacting with an inner surface of the locking element,
wherein the driving unit is configured to move the driving element to engage the movable locking element, wherein the moveable locking element is axially moved by the driving element in the distal closed end direction to release the at least one flexible part from the movable locking element, and wherein releasing the at least one flexible part from the movable locking element enables a disconnection of the first unit and the second unit, and
wherein the second distal connecting end of the housing has a longitudinal cross-section shape of varying dimensions and an extension formed at the end of an outer surface of the second distal connecting end.

2. The medicament delivery device according to claim 1, wherein the locking element is one of a separate axially movable element and a locking element integrated with the open connecting proximate end of the first unit.

3. The medicament delivery device according to claim 1, wherein the at least one flexible part is one of an integral part of one of a frame and the second distal connecting end and a separate flexible part arranged on one of the open connecting proximate end and second distal connecting end.

4. The medicament delivery device according to claim 3, wherein at least one of the at least one flexible part is integrally arranged on the frame carrying the driving unit, the at least one flexible part is extending in the axial A direction towards the distal closed end and forming a receiving opening; the open connecting proximate end is integrated with the locking element surrounding the at least one flexible part and is axially movable by driving unit via the driving element relative the housing allowing a first inserting and locking state of the open connecting proximate end and second distal connecting end and a second release state of the open connecting proximate end and second distal connecting end relative to each other.

5. The medicament delivery device according to claim 4, wherein in the first inserting and locking state of the device, the open connecting proximate end with the locking element is axially movable by the driving unit via the driving element in direction to the distal closed end allowing radially and outwardly movement of the at least one flexible part relative to the axis A releasing the wedge-shaped extensions of the flexible element from interacting with the inner surface of the locking element and insertion of the second connection end with the circular extension into the receiving opening; wherein springs situated between the movable open connecting proximate end and the frame are compressed; the driving unit is controlled to react on the second distal connecting end insertion allowing the movement of the open connecting proximate end by the springs in the opposite to the closed end axial direction so as to perform a snap-locking of the open connecting proximate end and second distal connecting end relative to each other; and in the second release state of the device, the driving unit is controlled to react by moving the open connecting proximate end in direction towards the closed end allowing the at least one flexible part flexing outwardly relative to the axis A thus releasing the open connecting proximate end and second distal connecting end of the units from connection with each other.

6. The medicament delivery device according to claim 1, wherein the at least one flexible part is integrally arranged on the second distal connecting end which is to be inserted into a receiving opening in the open connecting proximate end; the receiving opening is provided with a longitudinal cross-section shape of a various radial dimensions on its inner surface adapted to accommodate the at least one flexible part having a corresponding longitudinal cross-section on its outer surface and allowing in a first state of the device an inserting and locking of the open connecting proximate end and second distal connecting end relative to each other and in a second state of the device a releasing of the open connecting proximate end and second distal connecting end relative to each other.

7. The medicament delivery device according to claim 6, wherein the at least one flexible part having an outwardly extending ledge at its distal end is provided as an integral part of the housing, the housing having the second distal connecting end with an axial opening; the second distal connecting end is adapted to be inserted into the receiving opening of the open connecting proximate end having inclined wall surfaces and a groove able to accommodate the outwardly extending ledge for snap-locking the open connecting proximate end and second distal connecting end relative to each other.

8. The medicament delivery device according to claim 7, wherein in the first inserting and locking state of the device, when the second distal connecting end is to be inserted into the opening, wherein the outwardly extending ledge is guided along the inclined surfaces forcing the at least one flexible part to move radially and inwardly pressing by its outer edge the locking element axially loaded by a spring in the open connecting proximate end direction until the outwardly extending ledge been accommodated by the groove allowing the at least one flexible part move radially and outwardly relative to the axis A so as to snap lock the housing relative the housing; simultaneously expanded outwardly the at least one flexible part stopping pressure on the element so as the spring is released and pushing the locking element axially in the housing direction entering into the opening on the second distal connecting end, so as to press outwardly on the at least one flexible part when the at least one flexible part is interacting with the surfaces of the opening in the open connecting proximate end, preventing disassembling of the open connecting proximate end and second distal connecting end; in the second releasing state of the device, when the locking element is axially moved by the driving element in the distal closed end direction, the at least one flexible part is released from being pressured to the open connecting proximate end inner surface allowing the at least one flexible part to move radially and inwardly towards the axis A and thus disconnecting the open connecting proximate end and second distal connecting end from each other.

9. The medicament delivery device according to claim 1, wherein the at least one flexible part is made as a separate element with at least two ledges and arranged on the second distal connecting end; a receiving opening in the open connecting proximate end is provided in a holder inserted into the housing of the open connecting proximate end as a separate element and the locking element inserted into the holder between the holder and the flexible element; the opening is provided in the holder and has the inner surface adapted to guide and accommodate the at least one flexible part and allowing in a first state of the device an inserting and locking of the second distal connecting end relative to the open connecting proximate end and in a second state releasing of the second distal connecting end relative to the open connecting proximate end.

10. The medicament delivery device according to claim 9, wherein the at least one flexible part has at least two outwardly extending ledges for interaction with at least two slits into the holder; in the first inserting and locking state of the device, the second distal connecting end of the housing is inserted into the holder of the housing and forces the at least one flexible part along the guiding surface of the opening in the holder axially towards the closed end of the housing against a spring loading the locking element axially in the open connecting proximate end direction, when the at least two outwardly extending ledges are accommodated by the slits providing a snap-connection of the open connecting proximate end and second distal connecting end due to flexing outwards relative to the axis A, the movable locking element is moved axially by the spring in the direction of the open connecting proximate end preventing the at least two outwardly extending ledges movement radially and inwardly relative to the axis A and thus locking the open connecting proximate end and second distal connecting end relative to each other; in a second disconnecting state, the locking element is moved axially by the driving element in the direction of the distal closed end of the housing releasing the at least one flexible part and allowing the at least two outwardly ledges move radially and inwardly relative to the axis A allowing the disconnection of the open connecting proximate end and second distal connecting end.

11. The medicament delivery device according to claim 1, wherein a first inserting and locking state of the device can be achieved in one single stage or two separate stages.

12. The medicament delivery device according to claim 1, wherein the driving element is a plunger rod reciprocatingly movable by the driving unit via a transmission so as to interact with the medicament container for performing an injection and locking a snap connection of the open connecting proximate end and second distal connecting end of the device by the locking element and releasing the first unit and the second unit connection after the injection is completed.

13. The medicament delivery device according to claim 1, wherein the driving unit comprises one of a mechanical, a pneumatic, and an electrical driving device.

14. The medicament delivery device according to claim 1, wherein the medicament container is one of a syringe and a cartridge.

15. A medicament delivery device having an axis A, the delivery device comprising:
a first unit having a distal closed end and an open connecting proximate end, the open connecting proximate end comprising a driving unit with a driving element that moves in a reciprocating fashion; and
a second unit with a housing adapted to receive a medicament container and having a first proximal medicament delivery end and a second distal connecting end, where the second distal connecting end is adapted to be connected with the open proximate connecting end by insertion of the second connecting end into the open connecting proximate end along the axis A,
wherein one of the open connecting proximate end and second distal connecting end is equipped with a flexible part that moves radially inwards and outwards relative to the axis A due to force created by the insertion of the second distal connecting end into the open connecting proximate end and a movable locking element arranged within the first unit coaxially and configured to interact with the flexible part due to a relative axial movement of the flexible part and the locking element so as to lock the open connecting proximate end and second distal connecting end of the device relative to each other,
wherein the locking element is one of a separate axially movable element and a locking element integrated with the open connecting proximate end,
wherein the driving unit is configured to move the driving element to engage the locking element, wherein the moveable locking element is axially moved by the driving element in the distal closed end direction to release the at least one flexible part from the movable locking element, and wherein releasing the flexible part from the locking element enables a disconnection of the first unit and the second unit,
wherein the flexible part is one of an integral part of one of a frame and the second distal connecting end and a separate flexible part arranged on the open connecting proximate end, and
wherein a first inserting and locking state of the device can be achieved in one single stage.

16. The medicament delivery device according to claim 15, wherein the flexible part has a wedge-shaped guiding extension on its outer surface interacting with an inner surface of the locking element.

17. The medicament delivery device according to claim 16, wherein the second distal connecting end of the housing has a longitudinal cross-section shape of varying dimensions and an extension is formed at the end of an outer surface of the second distal connecting end.

18. The medicament delivery device according to claim 17, wherein the driving element is a plunger rod reciprocatingly movable by a mechanical driving unit via a transmission so as to interact with the medicament container for performing an injection and locking a snap connection of one of the open connecting proximate end and the second distal connecting end of the device by the locking element and releasing a housing connection after the injection is completed.

\* \* \* \* \*